United States Patent
Kim et al.

(10) Patent No.: US 8,895,807 B2
(45) Date of Patent: Nov. 25, 2014

(54) RABG3B GENE AND PROTEIN THEREOF FOR REGULATING LATE STAGE XYLEM DEVELOPMENT, METHOD FOR PROMOTING PLANT BIOMASS AND TRANSGENIC PLANT COMPRISING THE SAME

(75) Inventors: Ok-Mae Kim, Seoul (KR); Soon-Il Kwon, Gunpo Gyeonggi-Do (KR); Hong-Joo Cho, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 453 days.

(21) Appl. No.: 13/012,601

(22) Filed: Jan. 24, 2011

(65) Prior Publication Data

US 2012/0054916 A1 Mar. 1, 2012

(30) Foreign Application Priority Data

Sep. 1, 2010 (KR) .................. 10-2010-0085609

(51) Int. Cl.
*C12N 15/82* (2006.01)
*C12N 15/87* (2006.01)
*A01H 1/00* (2006.01)
*C07K 14/415* (2006.01)

(52) U.S. Cl.
CPC .......... *C12N 15/8261* (2013.01); *C07K 14/415* (2013.01)
USPC ....................................................... 800/290

(58) Field of Classification Search
USPC ......................................................... 800/290
See application file for complete search history.

(56) References Cited

PUBLICATIONS

Kwon et al. (Role of an Arabidopsis Rab GTPase RabG3b in Pathogen Response and Leaf Senescence, 52 J Plant Bio., 79-87 (2009); of record IDS Jul. 17, 2012).*
Chen et al., Complete sequence of the binary vector pBI121 and its application in cloning T-DNA insertion from transgenic plants, 11 Mol Breeding, 287-293 (2003)).*
UniProtKB page for O04157, available at http://www.uniprot.org/uniprot/O04157, accessed Oct. 24, 2013.*
TAIR page for At1g22740.1, available at http://www.arabidopsis.org/servlets/TairObject?type=gene&id=138315, accessed Oct. 24, 2013.*
Nieminen et al., A weed for wood? Arabidopsis as a genetic model for xylem development, 135 Plant Physiology, 653-659 (2004)).*
Kwon, S.I., et al., "Role of an Arabidopsis Rab GTPase RabG3b in Pathogen Response and Leaf Senescence," J. Plant Biol. (2009) 52: 79-87.

* cited by examiner

*Primary Examiner* — Ashwin Mehta
*Assistant Examiner* — Rebecca Coobs
(74) *Attorney, Agent, or Firm* — Edwards Wildman Palmer LLP; Kongsik Kim; Richard B. Emmons

(57) ABSTRACT

There are provided a method for promoting plant biomass by overexpression of a gene coding a small GTP binding protein RabG3b or mutants thereof, a vector including the gene, a transgenic plant comprising the expression vector and a method for preparing the transgenic plant.

4 Claims, 26 Drawing Sheets
(19 of 26 Drawing Sheet(s) Filed in Color)

FIG. 1
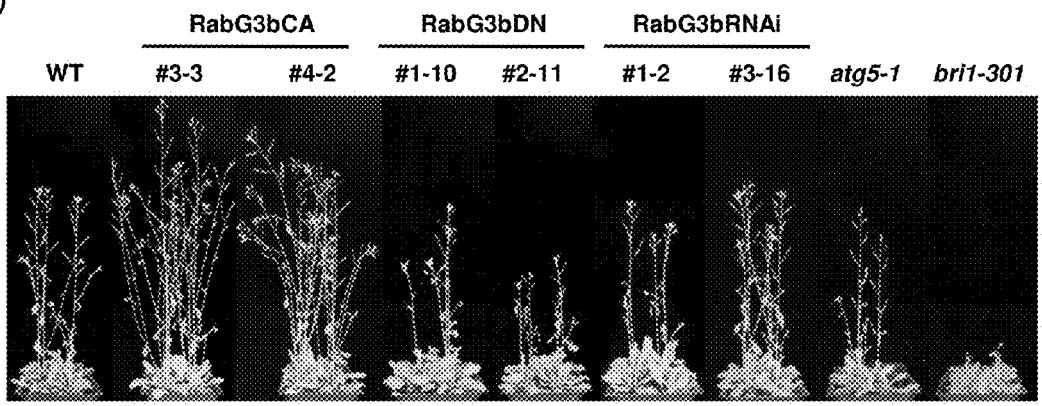
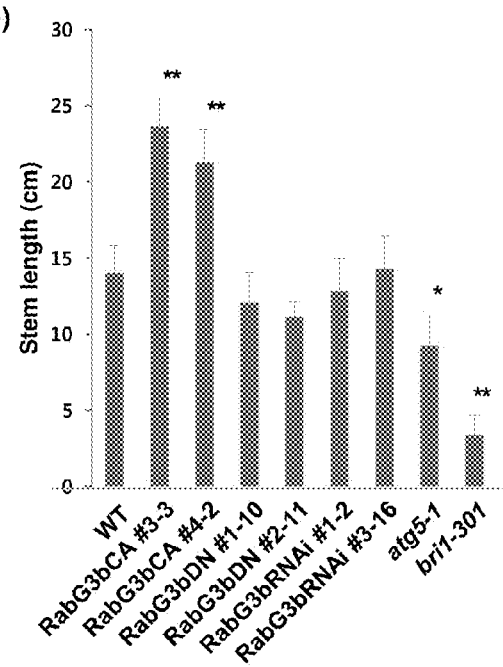
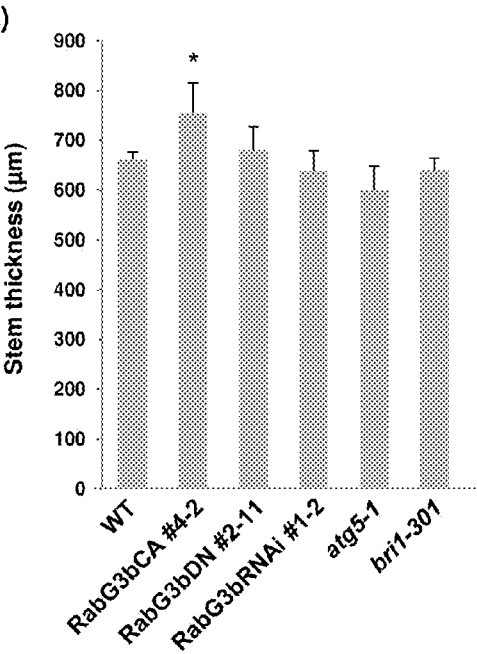

FIG. 11
(a)
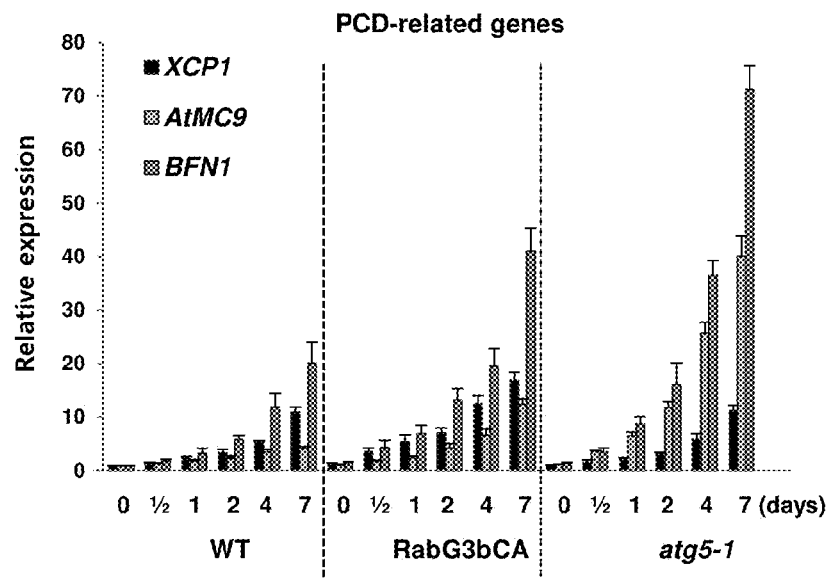
(b)
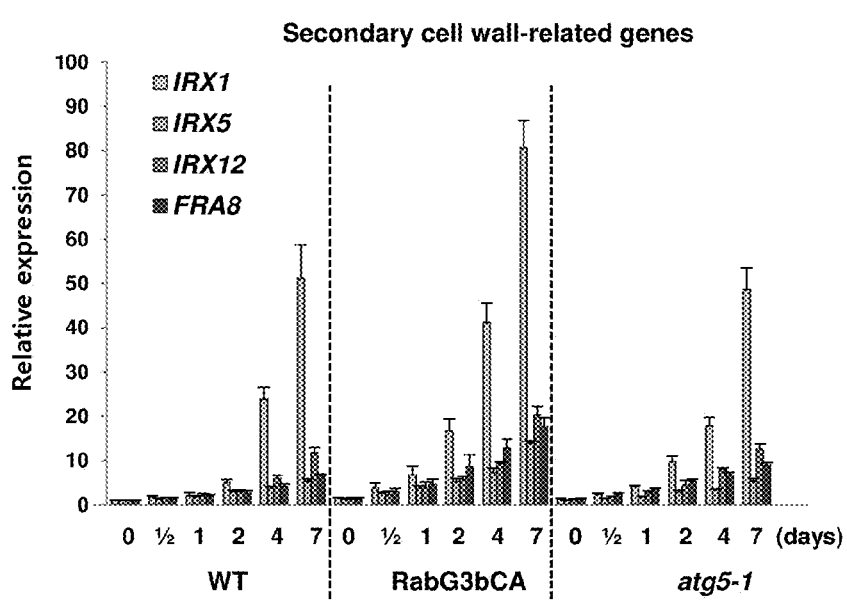

FIG. 13
(a)
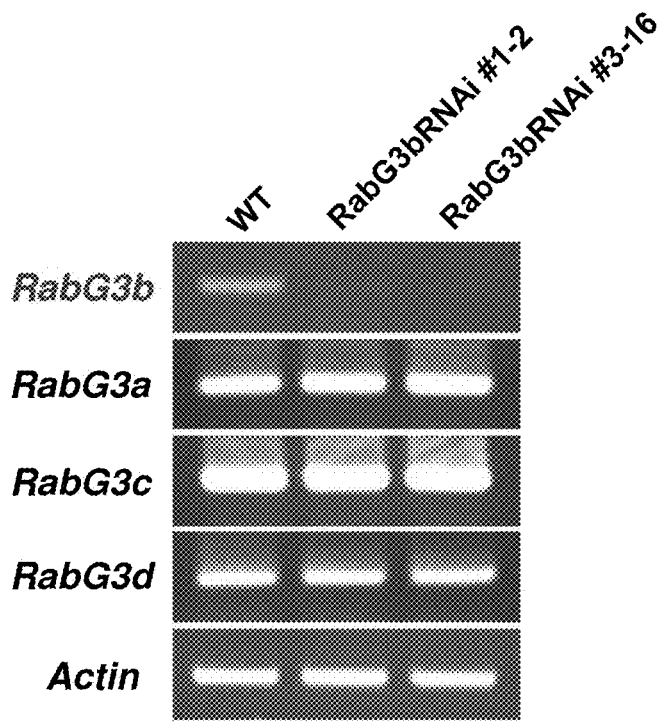
(b)
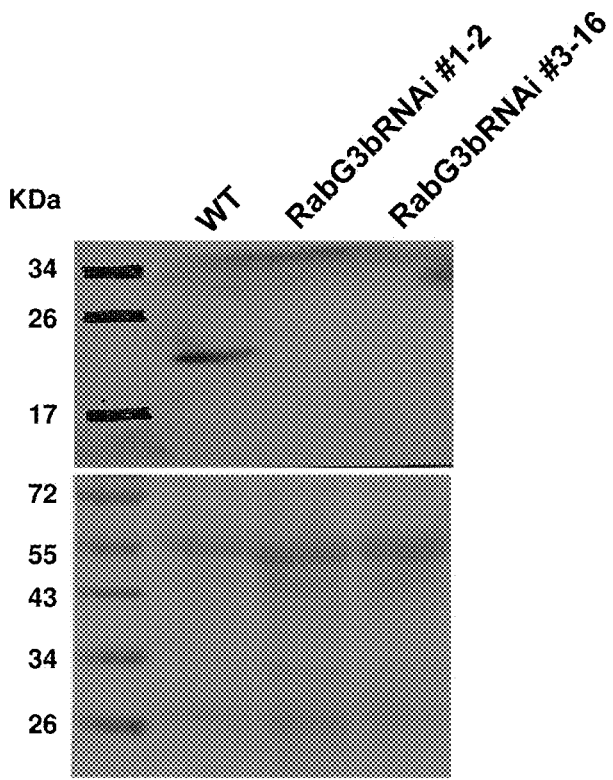

FIG. 23
(a)
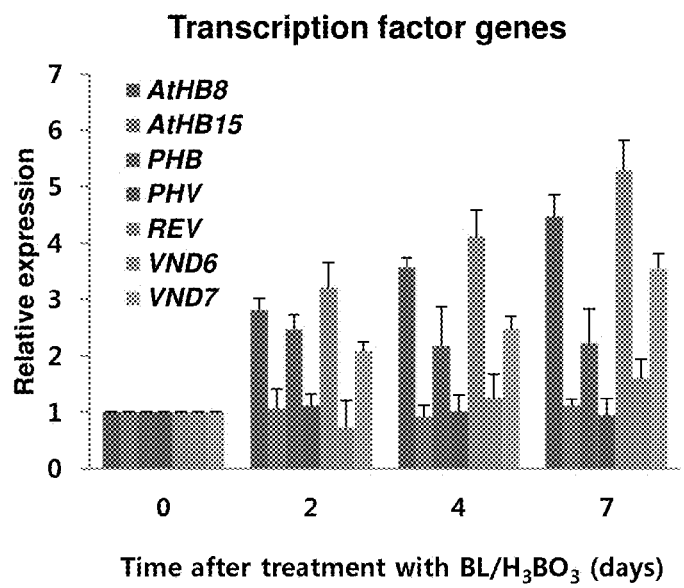
(b)
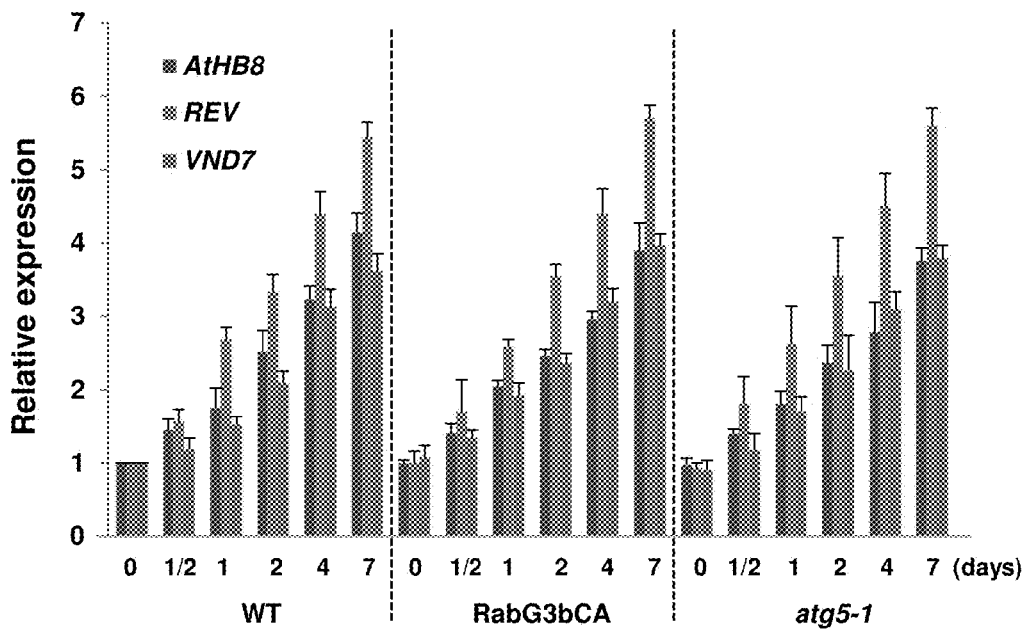

FIG. 24
(a)
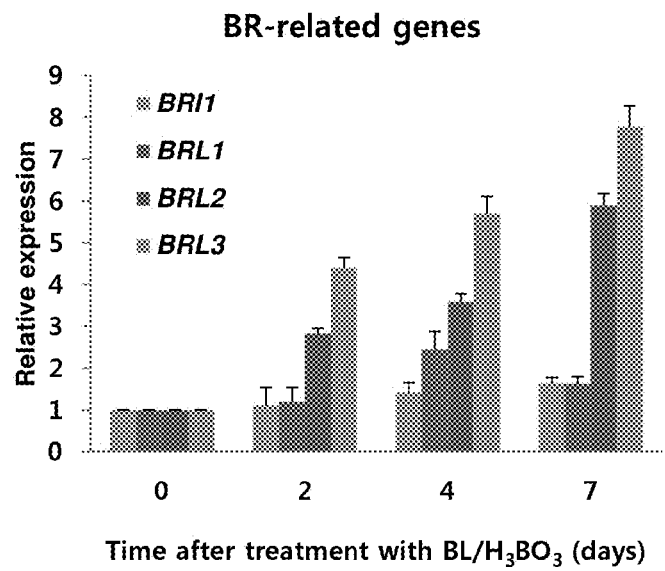
(b)
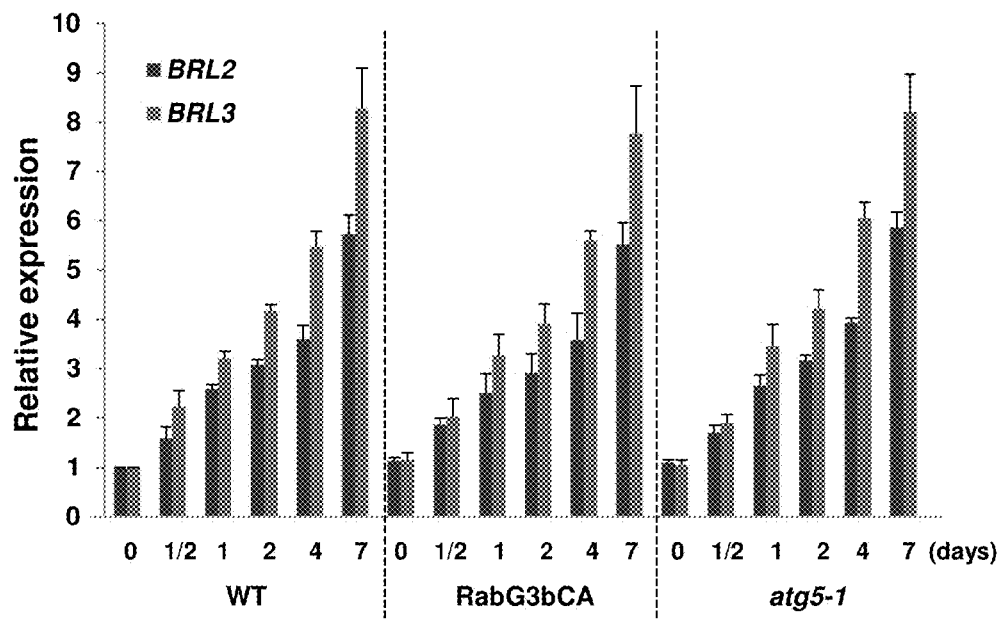

SEQUENCE LISTING

```
<160> NUMBER OF SEQ ID NOS: 93

<210> SEQ ID NO 1
<211> LENGTH: 203
<212> TYPE: PRT
<213> ORGANISM: Arabidopsis thaliana

<400> SEQUENCE: 1

Met Ser Thr Arg Arg Thr Leu Leu Lys Val Ile Ile Leu Gly Asp
1               5                   10                  15

Ser Gly Val Gly Lys Thr Ser Leu Met Asn Gln Tyr Val Asn Asn Lys
                20                  25                  30

Phe Ser Gln Gln Tyr Lys Ala Thr Ile Gly Ala Asp Phe Val Thr Lys
            35                  40                  45

Glu Leu Gln Ile Asp Asp Arg Leu Val Thr Leu Gln Ile Trp Asp Thr
        50                  55                  60

Ala Gly Gln Glu Arg Phe Gln Ser Leu Gly Val Ala Phe Tyr Arg Gly
65                  70                  75                  80

Ala Asp Cys Cys Val Leu Val Tyr Asp Val Asn His Leu Lys Ser Phe
                85                  90                  95

Glu Ser Leu Asp Asn Trp His Asn Glu Phe Leu Thr Arg Ala Ser Pro
```

```
            100                 105                 110
Arg Asp Pro Met Ala Phe Pro Phe Ile Leu Leu Gly Asn Lys Val Asp
            115                 120                 125

Ile Asp Gly Gly Asn Ser Arg Val Val Ser Glu Lys Lys Ala Arg Glu
        130                 135                 140

Trp Cys Ala Glu Lys Gly Asn Ile Val Tyr Phe Glu Thr Ser Ala Lys
145                 150                 155                 160

Glu Asp Tyr Asn Val Asp Asp Ser Phe Leu Cys Ile Thr Lys Leu Ala
                165                 170                 175

Leu Ala Asn Glu Arg Asp Gln Asp Ile Tyr Phe Gln Pro Asp Thr Gly
            180                 185                 190

Ser Val Pro Glu Gln Arg Gly Gly Cys Ala Cys
            195                 200

<210> SEQ ID NO 2
<211> LENGTH: 609
<212> TYPE: DNA
<213> ORGANISM: Arabidopsis thaliana

<400> SEQUENCE: 2
atgtcgacgc gaagacgaac tttactcaaa gttataattc ttggagacag cggggttggc    60
aaaacatcgt tgatgaatca atatgtgaat aacaagttta gtcaacagta caaagctacg   120
atcggagctg attttgtcac taaggagctt caaattgatg acaggcttgt cacattgcaa   180
atatgggaca ctgctgggca agagaggttt caaagtcttg gtgttgcttt ctatagaggt   240
gcagattgtt gtgttcttgt ctatgatgtg aatcacttga agtcatttga atctctcgac   300
aattggcaca acgagtttct tacacgggct agtccacgtg acccaatggc attccctttt   360
atacttcttg gtaataaggt tgatattgat ggaggaaata gccgagtggt atctgagaag   420
aaggctagag aatggtgtgc tgaaaaggga acatagtcta tttcgagac atcggctaaa    480 gaagattaca atgtcgatga ctccttcttg tgcatcacaa aacttgccct tgcaaatgaa   540
cgcgaccaag atatatattt ccagccagat actggttcgg tgcctgagca agaggaggt    600 tgtgcttgc                                                           609

<210> SEQ ID NO 3
<211> LENGTH: 609
<212> TYPE: DNA
<213> ORGANISM: Artificial Sequence
<220> FEATURE:
<223> OTHER INFORMATION: mutant

<400> SEQUENCE: 3
atgtcgacgc gaagacgaac tttactcaaa gttataattc ttggagacag cggggttggc    60
aaaacatcgt tgatgaatca atatgtgaat aacaagttta gtcaacagta caaagctacg   120
atcggagctg attttgtcac taaggagctt caaattgatg acaggcttgt cacattgcaa   180
atatgggaca ctgctgggct agagaggttt caaagtcttg gtgttgcttt ctatagaggt   240
gcagattgtt gtgttcttgt ctatgatgtg aatcacttga agtcatttga atctctcgac   300
aattggcaca acgagtttct tacacgggct agtccacgtg acccaatggc attccctttt   360
atacttcttg gtaataaggt tgatattgat ggaggaaata gccgagtggt atctgagaag   420
aaggctagag aatggtgtgc tgaaaaggga acatagtcta tttcgagac atcggctaaa    480 gaagattaca atgtcgatga ctccttcttg tgcatcacaa aacttgccct tgcaaatgaa   540
cgcgaccaag atatatattt ccagccagat actggttcgg tgcctgagca agaggaggt    600
```

| | |
|---|---|
| tgtgcttgc | 609 |

<210> SEQ ID NO 4
<211> LENGTH: 24
<212> TYPE: DNA
<213> ORGANISM: Artificial Sequence
<220> FEATURE:
<223> OTHER INFORMATION: Forward primer

<400> SEQUENCE: 4

| | |
|---|---|
| gataagaaag cagctgactg gtgt | 24 |

<210> SEQ ID NO 5
<211> LENGTH: 24
<212> TYPE: DNA
<213> ORGANISM: Artificial Sequence
<220> FEATURE:
<223> OTHER INFORMATION: Reverse primer

<400> SEQUENCE: 5

| | |
|---|---|
| gatcatacac agacttctcc aatc | 24 |

<210> SEQ ID NO 6
<211> LENGTH: 25
<212> TYPE: DNA
<213> ORGANISM: Artificial Sequence
<220> FEATURE:
<223> OTHER INFORMATION: Forward primer

<400> SEQUENCE: 6

| | |
|---|---|
| agaaggctag agaatggtgt gctga | 25 |

<210> SEQ ID NO 7
<211> LENGTH: 25
<212> TYPE: DNA
<213> ORGANISM: Artificial Sequence
<220> FEATURE:
<223> OTHER INFORMATION: Reverse primer

<400> SEQUENCE: 7

| | |
|---|---|
| catacaaatc gtgaaccacc aaatg | 25 |

<210> SEQ ID NO 8
<211> LENGTH: 25
<212> TYPE: DNA
<213> ORGANISM: Artificial Sequence
<220> FEATURE:
<223> OTHER INFORMATION: Forward primer

<400> SEQUENCE: 8

| | |
|---|---|
| agatggagtc aatgttgatg cagct | 25 |

<210> SEQ ID NO 9
<211> LENGTH: 25
<212> TYPE: DNA
<213> ORGANISM: Artificial Sequence
<220> FEATURE:
<223> OTHER INFORMATION: Reverse primer

<400> SEQUENCE: 9

| | |
|---|---|
| gaagattacg acaagctgaa gagat | 25 |

<210> SEQ ID NO 10
<211> LENGTH: 24
<212> TYPE: DNA

```
<213> ORGANISM: Artificial Sequence
<220> FEATURE:
<223> OTHER INFORMATION: Forward primer

<400> SEQUENCE: 10
cgccaaagaa ggattcaatg taga                                              24

<210> SEQ ID NO 11
<211> LENGTH: 24
<212> TYPE: DNA
<213> ORGANISM: Artificial Sequence
<220> FEATURE:
<223> OTHER INFORMATION: Reverse primer

<400> SEQUENCE: 11
gagtccaaaa gaaaaggaa ccca                                               24

<210> SEQ ID NO 12
<211> LENGTH: 23
<212> TYPE: DNA
<213> ORGANISM: Artificial Sequence
<220> FEATURE:
<223> OTHER INFORMATION: Forward primer

<400> SEQUENCE: 12
ggcgatgaag ctcaatccaa acg                                               23

<210> SEQ ID NO 13
<211> LENGTH: 25
<212> TYPE: DNA
<213> ORGANISM: Artificial Sequence
<220> FEATURE:
<223> OTHER INFORMATION: Reverse primer

<400> SEQUENCE: 13
ggtcacgacc agcaagatca agacg                                             25

<210> SEQ ID NO 14
<211> LENGTH: 22
<212> TYPE: DNA
<213> ORGANISM: Artificial Sequence
<220> FEATURE:
<223> OTHER INFORMATION: Forward primer

<400> SEQUENCE: 14
catcccaacg ctatcaaacc ta                                                22

<210> SEQ ID NO 15
<211> LENGTH: 22
<212> TYPE: DNA
<213> ORGANISM: Artificial Sequence
<220> FEATURE:
<223> OTHER INFORMATION: Reverse primer

<400> SEQUENCE: 15
gctgagacac ctccaataac cc                                                22

<210> SEQ ID NO 16
<211> LENGTH: 20
<212> TYPE: DNA
<213> ORGANISM: Artificial Sequence
<220> FEATURE:
<223> OTHER INFORMATION: Forward primer

<400> SEQUENCE: 16
tcggtggcat gatgaatttg                                                   20
```

-continued

```
<210> SEQ ID NO 17
<211> LENGTH: 27
<212> TYPE: DNA
<213> ORGANISM: Artificial Sequence
<220> FEATURE:
<223> OTHER INFORMATION: Reverse primer

<400> SEQUENCE: 17
cacatctata ccacttcttg cctactg                                              27

<210> SEQ ID NO 18
<211> LENGTH: 18
<212> TYPE: DNA
<213> ORGANISM: Artificial Sequence
<220> FEATURE:
<223> OTHER INFORMATION: Forward primer

<400> SEQUENCE: 18
tctgggtgat tggcggtg                                                        18

<210> SEQ ID NO 19
<211> LENGTH: 20
<212> TYPE: DNA
<213> ORGANISM: Artificial Sequence
<220> FEATURE:
<223> OTHER INFORMATION: Reverse primer

<400> SEQUENCE: 19
gtcggaggga tgagaagggt                                                      20

<210> SEQ ID NO 20
<211> LENGTH: 24
<212> TYPE: DNA
<213> ORGANISM: Artificial Sequence
<220> FEATURE:
<223> OTHER INFORMATION: Forward primer

<400> SEQUENCE: 20
cctaaggatc ttcccaagtg ctaa                                                 24

<210> SEQ ID NO 21
<211> LENGTH: 19
<212> TYPE: DNA
<213> ORGANISM: Artificial Sequence
<220> FEATURE:
<223> OTHER INFORMATION: Reverse primer

<400> SEQUENCE: 21
cttggacgtg gcgtgatgt                                                       19

<210> SEQ ID NO 22
<211> LENGTH: 20
<212> TYPE: DNA
<213> ORGANISM: Artificial Sequence
<220> FEATURE:
<223> OTHER INFORMATION: Forward primer

<400> SEQUENCE: 22
gaaaatggac cgcctcatga                                                      20

<210> SEQ ID NO 23
<211> LENGTH: 24
<212> TYPE: DNA
<213> ORGANISM: Artificial Sequence
<220> FEATURE:
```

<223> OTHER INFORMATION: Reverse primer

<400> SEQUENCE: 23
tcatcgtggt tagcttcttc ttga        24

<210> SEQ ID NO 24
<211> LENGTH: 23
<212> TYPE: DNA
<213> ORGANISM: Artificial Sequence
<220> FEATURE:
<223> OTHER INFORMATION: Forward primer

<400> SEQUENCE: 24
ttcgaaacgc agtcgtataa tcc        23

<210> SEQ ID NO 25
<211> LENGTH: 27
<212> TYPE: DNA
<213> ORGANISM: Artificial Sequence
<220> FEATURE:
<223> OTHER INFORMATION: Reverse primer

<400> SEQUENCE: 25
attagcttcg acctcattat agctttg        27

<210> SEQ ID NO 26
<211> LENGTH: 20
<212> TYPE: DNA
<213> ORGANISM: Artificial Sequence
<220> FEATURE:
<223> OTHER INFORMATION: Forward primer

<400> SEQUENCE: 26
gttgtgcttt tgcccgtgat        20

<210> SEQ ID NO 27
<211> LENGTH: 25
<212> TYPE: DNA
<213> ORGANISM: Artificial Sequence
<220> FEATURE:
<223> OTHER INFORMATION: Reverse primer

<400> SEQUENCE: 27
gaagcttgtc agtgtttgtc aaatg        25

<210> SEQ ID NO 28
<211> LENGTH: 22
<212> TYPE: DNA
<213> ORGANISM: Artificial Sequence
<220> FEATURE:
<223> OTHER INFORMATION: Forward primer

<400> SEQUENCE: 28
ccacctccac gagctgacat tc        22

<210> SEQ ID NO 29
<211> LENGTH: 23
<212> TYPE: DNA
<213> ORGANISM: Artificial Sequence
<220> FEATURE:
<223> OTHER INFORMATION: Reverse primer

<400> SEQUENCE: 29
aaggaggagg cgatggacga ttc        23

```
<210> SEQ ID NO 30
<211> LENGTH: 20
<212> TYPE: DNA
<213> ORGANISM: Artificial Sequence
<220> FEATURE:
<223> OTHER INFORMATION: Forward primer

<400> SEQUENCE: 30
aggcagtcct tgaccacttg                                                     20

<210> SEQ ID NO 31
<211> LENGTH: 20
<212> TYPE: DNA
<213> ORGANISM: Artificial Sequence
<220> FEATURE:
<223> OTHER INFORMATION: Reverse primer

<400> SEQUENCE: 31
ccctgagtcc acgtgttttt                                                     20

<210> SEQ ID NO 32
<211> LENGTH: 22
<212> TYPE: DNA
<213> ORGANISM: Artificial Sequence
<220> FEATURE:
<223> OTHER INFORMATION: Forward primer

<400> SEQUENCE: 32
tgccacactg ggcatagaag at                                                  22

<210> SEQ ID NO 33
<211> LENGTH: 22
<212> TYPE: DNA
<213> ORGANISM: Artificial Sequence
<220> FEATURE:
<223> OTHER INFORMATION: Reverse primer

<400> SEQUENCE: 33
tccagttaca cgagccattt ca                                                  22

<210> SEQ ID NO 34
<211> LENGTH: 20
<212> TYPE: DNA
<213> ORGANISM: Artificial Sequence
<220> FEATURE:
<223> OTHER INFORMATION: Forward primer

<400> SEQUENCE: 34
attctgaatc cgccactgtc                                                     20

<210> SEQ ID NO 35
<211> LENGTH: 20
<212> TYPE: DNA
<213> ORGANISM: Artificial Sequence
<220> FEATURE:
<223> OTHER INFORMATION: Reverse primer

<400> SEQUENCE: 35
gagaacccaa cccaagtgaa                                                     20

<210> SEQ ID NO 36
<211> LENGTH: 20
<212> TYPE: DNA
<213> ORGANISM: Artificial Sequence
<220> FEATURE:
<223> OTHER INFORMATION: Forward primer
```

<400> SEQUENCE: 36
gaaatatcag ccacggagga                                              20

<210> SEQ ID NO 37
<211> LENGTH: 20
<212> TYPE: DNA
<213> ORGANISM: Artificial Sequence
<220> FEATURE:
<223> OTHER INFORMATION: Reverse primer

<400> SEQUENCE: 37
gcaccgcttt tgagtagagg                                              20

<210> SEQ ID NO 38
<211> LENGTH: 20
<212> TYPE: DNA
<213> ORGANISM: Artificial Sequence
<220> FEATURE:
<223> OTHER INFORMATION: Forward primer

<400> SEQUENCE: 38
gaaacaagtg ctgccactca                                              20

<210> SEQ ID NO 39
<211> LENGTH: 20
<212> TYPE: DNA
<213> ORGANISM: Artificial Sequence
<220> FEATURE:
<223> OTHER INFORMATION: Reverse primer

<400> SEQUENCE: 39
aatccgcttc ttgtcgtcag                                              20

<210> SEQ ID NO 40
<211> LENGTH: 24
<212> TYPE: DNA
<213> ORGANISM: Artificial Sequence
<220> FEATURE:
<223> OTHER INFORMATION: Forward primer

<400> SEQUENCE: 40
ttaatcgccc tgttgagttc ctca                                         24

<210> SEQ ID NO 41
<211> LENGTH: 24
<212> TYPE: DNA
<213> ORGANISM: Artificial Sequence
<220> FEATURE:
<223> OTHER INFORMATION: Reverse primer

<400> SEQUENCE: 41
taccacccac gaaaacggta tctc                                         24

<210> SEQ ID NO 42
<211> LENGTH: 24
<212> TYPE: DNA
<213> ORGANISM: Artificial Sequence
<220> FEATURE:
<223> OTHER INFORMATION: Forward primer

<400> SEQUENCE: 42
ttgcaaattc aaaggaccaa gaga                                         24

<210> SEQ ID NO 43
<211> LENGTH: 24

```
<212> TYPE: DNA
<213> ORGANISM: Artificial Sequence
<220> FEATURE:
<223> OTHER INFORMATION: Reverse primer

<400> SEQUENCE: 43
agagagaccg tcgcagagag aggt                                          24

<210> SEQ ID NO 44
<211> LENGTH: 20
<212> TYPE: DNA
<213> ORGANISM: Artificial Sequence
<220> FEATURE:
<223> OTHER INFORMATION: Forward primer

<400> SEQUENCE: 44
gtaccgcttg ctctgaaacc                                               20

<210> SEQ ID NO 45
<211> LENGTH: 20
<212> TYPE: DNA
<213> ORGANISM: Artificial Sequence
<220> FEATURE:
<223> OTHER INFORMATION: Reverse primer

<400> SEQUENCE: 45
gtcttcccag tcgaggttga                                               20

<210> SEQ ID NO 46
<211> LENGTH: 24
<212> TYPE: DNA
<213> ORGANISM: Artificial Sequence
<220> FEATURE:
<223> OTHER INFORMATION: Forward primer

<400> SEQUENCE: 46
ggagaaggct ggacaaagtg atgt                                          24

<210> SEQ ID NO 47
<211> LENGTH: 24
<212> TYPE: DNA
<213> ORGANISM: Artificial Sequence
<220> FEATURE:
<223> OTHER INFORMATION: Reverse primer

<400> SEQUENCE: 47
tagatcgcag acatcaatgc agca                                          24

<210> SEQ ID NO 48
<211> LENGTH: 24
<212> TYPE: DNA
<213> ORGANISM: Artificial Sequence
<220> FEATURE:
<223> OTHER INFORMATION: Forward primer

<400> SEQUENCE: 48
accctgatcg aattcctgtg attg                                          24

<210> SEQ ID NO 49
<211> LENGTH: 24
<212> TYPE: DNA
<213> ORGANISM: Artificial Sequence
<220> FEATURE:
<223> OTHER INFORMATION: Reverse primer

<400> SEQUENCE: 49
```
agctctcctg ttggaggaag aaca 24

<210> SEQ ID NO 50
<211> LENGTH: 24
<212> TYPE: DNA
<213> ORGANISM: Artificial Sequence
<220> FEATURE:
<223> OTHER INFORMATION: Forward primer

<400> SEQUENCE: 50
accggagcga tgatgtcaac catt 24

<210> SEQ ID NO 51
<211> LENGTH: 24
<212> TYPE: DNA
<213> ORGANISM: Artificial Sequence
<220> FEATURE:
<223> OTHER INFORMATION: Reverse primer

<400> SEQUENCE: 51
tgcaaaccga ttggttgtgc ctac 24

<210> SEQ ID NO 52
<211> LENGTH: 20
<212> TYPE: DNA
<213> ORGANISM: Artificial Sequence
<220> FEATURE:
<223> OTHER INFORMATION: Forward primer

<400> SEQUENCE: 52
cccaaccatg gaaaatgaag 20

<210> SEQ ID NO 53
<211> LENGTH: 20
<212> TYPE: DNA
<213> ORGANISM: Artificial Sequence
<220> FEATURE:
<223> OTHER INFORMATION: Reverse primer

<400> SEQUENCE: 53
gaaccatggc ctgttcaaat 20

<210> SEQ ID NO 54
<211> LENGTH: 20
<212> TYPE: DNA
<213> ORGANISM: Artificial Sequence
<220> FEATURE:
<223> OTHER INFORMATION: Forward primer

<400> SEQUENCE: 54
gcatggggct aaaactgaag 20

<210> SEQ ID NO 55
<211> LENGTH: 20
<212> TYPE: DNA
<213> ORGANISM: Artificial Sequence
<220> FEATURE:
<223> OTHER INFORMATION: Reverse primer

<400> SEQUENCE: 55
gccgacggaa aaatacaaag 20

<210> SEQ ID NO 56
<211> LENGTH: 24
<212> TYPE: DNA
<213> ORGANISM: Artificial Sequence
<220> FEATURE:
<223> OTHER INFORMATION: Forward primer

<400> SEQUENCE: 56
tttggaccat cgacacagct tcca                                   24

<210> SEQ ID NO 57
<211> LENGTH: 24
<212> TYPE: DNA
<213> ORGANISM: Artificial Sequence
<220> FEATURE:
<223> OTHER INFORMATION: Reverse primer

<400> SEQUENCE: 57
actgcgtttt gaagcacatg atga                                   24

<210> SEQ ID NO 58
<211> LENGTH: 24
<212> TYPE: DNA
<213> ORGANISM: Artificial Sequence
<220> FEATURE:
<223> OTHER INFORMATION: Forward primer

<400> SEQUENCE: 58
tgaccttgac attggatggc ttgc                                   24

<210> SEQ ID NO 59
<211> LENGTH: 24
<212> TYPE: DNA
<213> ORGANISM: Artificial Sequence
<220> FEATURE:
<223> OTHER INFORMATION: Reverse primer

<400> SEQUENCE: 59
ttgatactgc aagccactgc acgt                                   24

<210> SEQ ID NO 60
<211> LENGTH: 24
<212> TYPE: DNA
<213> ORGANISM: Artificial Sequence
<220> FEATURE:
<223> OTHER INFORMATION: Forward primer

<400> SEQUENCE: 60
acgctcatgt cttgccaaag aacg                                   24

<210> SEQ ID NO 61
<211> LENGTH: 24
<212> TYPE: DNA
<213> ORGANISM: Artificial Sequence
<220> FEATURE:
<223> OTHER INFORMATION: Reverse primer

<400> SEQUENCE: 61
tttcattgga gaccacctcc tcga                                   24

<210> SEQ ID NO 62
<211> LENGTH: 24
<212> TYPE: DNA
<213> ORGANISM: Artificial Sequence
<220> FEATURE:
<223> OTHER INFORMATION: Forward primer

<400> SEQUENCE: 62
agacacctgg acaacctcct cctt                                   24

<210> SEQ ID NO 63
<211> LENGTH: 24
<212> TYPE: DNA
<213> ORGANISM: Artificial Sequence
<220> FEATURE:
<223> OTHER INFORMATION: Reverse primer

<400> SEQUENCE: 63
ggaatagttg aacccgccat gaga                                           24

<210> SEQ ID NO 64
<211> LENGTH: 20
<212> TYPE: DNA
<213> ORGANISM: Artificial Sequence
<220> FEATURE:
<223> OTHER INFORMATION: Forward primer

<400> SEQUENCE: 64
tgaagtcccc caattagcac                                                20

<210> SEQ ID NO 65
<211> LENGTH: 20
<212> TYPE: DNA
<213> ORGANISM: Artificial Sequence
<220> FEATURE:
<223> OTHER INFORMATION: Reverse primer

<400> SEQUENCE: 65
acggcacgct catttaaaac                                                20

<210> SEQ ID NO 66
<211> LENGTH: 20
<212> TYPE: DNA
<213> ORGANISM: Artificial Sequence
<220> FEATURE:
<223> OTHER INFORMATION: Forward primer

<400> SEQUENCE: 66
gattcaccgg attttggaga                                                20

<210> SEQ ID NO 67
<211> LENGTH: 20
<212> TYPE: DNA
<213> ORGANISM: Artificial Sequence
<220> FEATURE:
<223> OTHER INFORMATION: Reverse primer

<400> SEQUENCE: 67
gacccggctt gtatctcctt                                                20

<210> SEQ ID NO 68
<211> LENGTH: 20
<212> TYPE: DNA
<213> ORGANISM: Artificial Sequence
<220> FEATURE:
<223> OTHER INFORMATION: Forward primer

<400> SEQUENCE: 68
ttgatccgga gcttgtaacc                                                20

<210> SEQ ID NO 69
<211> LENGTH: 20
<212> TYPE: DNA
<213> ORGANISM: Artificial Sequence
<220> FEATURE:
<223> OTHER INFORMATION: Reverse primer

<400> SEQUENCE: 69
ccttatctcg cgattcttcg                                            20

<210> SEQ ID NO 70
<211> LENGTH: 20
<212> TYPE: DNA
<213> ORGANISM: Artificial Sequence
<220> FEATURE:
<223> OTHER INFORMATION: Forward primer

<400> SEQUENCE: 70
cgagactgat cagcgcatta                                            20

<210> SEQ ID NO 71
<211> LENGTH: 20
<212> TYPE: DNA
<213> ORGANISM: Artificial Sequence
<220> FEATURE:
<223> OTHER INFORMATION: Reverse primer

<400> SEQUENCE: 71
tttcccttct cttgccttca                                            20

<210> SEQ ID NO 72
<211> LENGTH: 20
<212> TYPE: DNA
<213> ORGANISM: Artificial Sequence
<220> FEATURE:
<223> OTHER INFORMATION: Forward primer

<400> SEQUENCE: 72
gagctcctct caggcaagaa                                            20

<210> SEQ ID NO 73
<211> LENGTH: 20
<212> TYPE: DNA
<213> ORGANISM: Artificial Sequence
<220> FEATURE:
<223> OTHER INFORMATION: Reverse primer

<400> SEQUENCE: 73
cgatcgtcca aacattgaga                                            20

<210> SEQ ID NO 74
<211> LENGTH: 20
<212> TYPE: DNA
<213> ORGANISM: Artificial Sequence
<220> FEATURE:
<223> OTHER INFORMATION: Forward primer

<400> SEQUENCE: 74
aatcattcct tccggtttcc                                            20

<210> SEQ ID NO 75
<211> LENGTH: 20
<212> TYPE: DNA
<213> ORGANISM: Artificial Sequence
<220> FEATURE:
<223> OTHER INFORMATION: Reverse primer

<400> SEQUENCE: 75
cgacgcgatc acacttctta                                            20

<210> SEQ ID NO 76

```
<211> LENGTH: 20
<212> TYPE: DNA
<213> ORGANISM: Artificial Sequence
<220> FEATURE:
<223> OTHER INFORMATION: Forward primer

<400> SEQUENCE: 76
gcgggatatg tctctcaagc                                               20

<210> SEQ ID NO 77
<211> LENGTH: 20
<212> TYPE: DNA
<213> ORGANISM: Artificial Sequence
<220> FEATURE:
<223> OTHER INFORMATION: Reverse primer

<400> SEQUENCE: 77
tacagccaaa aggcaaaagc                                               20

<210> SEQ ID NO 78
<211> LENGTH: 20
<212> TYPE: DNA
<213> ORGANISM: Artificial Sequence
<220> FEATURE:
<223> OTHER INFORMATION: Forward primer

<400> SEQUENCE: 78
gcttcaccgg ttttcacatt                                               20

<210> SEQ ID NO 79
<211> LENGTH: 20
<212> TYPE: DNA
<213> ORGANISM: Artificial Sequence
<220> FEATURE:
<223> OTHER INFORMATION: Reverse primer

<400> SEQUENCE: 79
agaactttcc acaccgttgc                                               20

<210> SEQ ID NO 80
<211> LENGTH: 20
<212> TYPE: DNA
<213> ORGANISM: Artificial Sequence
<220> FEATURE:
<223> OTHER INFORMATION: Forward primer

<400> SEQUENCE: 80
cttccggcag gaatatgtgt                                               20

<210> SEQ ID NO 81
<211> LENGTH: 20
<212> TYPE: DNA
<213> ORGANISM: Artificial Sequence
<220> FEATURE:
<223> OTHER INFORMATION: Reverse primer

<400> SEQUENCE: 81
gccaaaaaca acatcccta                                                20

<210> SEQ ID NO 82
<211> LENGTH: 20
<212> TYPE: DNA
<213> ORGANISM: Artificial Sequence
<220> FEATURE:
<223> OTHER INFORMATION: Forward primer

<400> SEQUENCE: 82
```
attcacttgg aagcgacgac					20

<210> SEQ ID NO 83
<211> LENGTH: 20
<212> TYPE: DNA
<213> ORGANISM: Artificial Sequence
<220> FEATURE:
<223> OTHER INFORMATION: Reverse primer

<400> SEQUENCE: 83
gcgaagtccg aacagatagc					20

<210> SEQ ID NO 84
<211> LENGTH: 21
<212> TYPE: DNA
<213> ORGANISM: Artificial Sequence
<220> FEATURE:
<223> OTHER INFORMATION: Forward primer

<400> SEQUENCE: 84
gacttgttga atcggtggct c					21

<210> SEQ ID NO 85
<211> LENGTH: 21
<212> TYPE: DNA
<213> ORGANISM: Artificial Sequence
<220> FEATURE:
<223> OTHER INFORMATION: Reverse primer

<400> SEQUENCE: 85
gaaagagttt gaccttctaa c					21

<210> SEQ ID NO 86
<211> LENGTH: 21
<212> TYPE: DNA
<213> ORGANISM: Artificial Sequence
<220> FEATURE:
<223> OTHER INFORMATION: Forward primer

<400> SEQUENCE: 86
tcgttgatgc tgacaaagac a					21

<210> SEQ ID NO 87
<211> LENGTH: 20
<212> TYPE: DNA
<213> ORGANISM: Artificial Sequence
<220> FEATURE:
<223> OTHER INFORMATION: Reverse primer

<400> SEQUENCE: 87
actgatccga cggcagatag					20

<210> SEQ ID NO 88
<211> LENGTH: 21
<212> TYPE: DNA
<213> ORGANISM: Artificial Sequence
<220> FEATURE:
<223> OTHER INFORMATION: Forward primer

<400> SEQUENCE: 88
ggttacctca acaatccggc a					21

<210> SEQ ID NO 89
<211> LENGTH: 21
<212> TYPE: DNA

```
<213> ORGANISM: Artificial Sequence
<220> FEATURE:
<223> OTHER INFORMATION: Reverse primer

<400> SEQUENCE: 89
caaatgcaac aggaacttca c                                              21

<210> SEQ ID NO 90
<211> LENGTH: 21
<212> TYPE: DNA
<213> ORGANISM: Artificial Sequence
<220> FEATURE:
<223> OTHER INFORMATION: Forward primer

<400> SEQUENCE: 90
cgtggacaga atgcaacgat c                                              21

<210> SEQ ID NO 91
<211> LENGTH: 21
<212> TYPE: DNA
<213> ORGANISM: Artificial Sequence
<220> FEATURE:
<223> OTHER INFORMATION: Reverse primer

<400> SEQUENCE: 91
accagcaata gcatgatcgt c                                              21

<210> SEQ ID NO 92
<211> LENGTH: 17
<212> TYPE: DNA
<213> ORGANISM: Artificial Sequence
<220> FEATURE:
<223> OTHER INFORMATION: Forward primer

<400> SEQUENCE: 92
gacgcttcat ctcgtcc                                                   17

<210> SEQ ID NO 93
<211> LENGTH: 19
<212> TYPE: DNA
<213> ORGANISM: Artificial Sequence
<220> FEATURE:
<223> OTHER INFORMATION: Reverse primer

<400> SEQUENCE: 93
gtaaacgtag gtgagtcca                                                 19
```

RABG3B GENE AND PROTEIN THEREOF FOR REGULATING LATE STAGE XYLEM DEVELOPMENT, METHOD FOR PROMOTING PLANT BIOMASS AND TRANSGENIC PLANT COMPRISING THE SAME

CROSS-REFERENCE TO RELATED APPLICATIONS

This application claims the priority of Korean Patent Application No. 2010-0085609 filed on Sep. 1, 2010, in the Korean Intellectual Property Office, the disclosure of which is incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 30, 2014, is named 87958-302663_ST25.txt and is 20,954 bytes in size.

BACKGROUND OF THE INVENTION

1. Field of the Invention

The present invention relates to a method for promoting plant biomass by overexpression of a small GTP binding protein RabG3b, a vector including the relevant gene, a transgenic plant including the vector and a method for producing the same.

2. Description of the Related Art

In general, specifically modified plants may be acquired using molecular technology in agriculture, gardening, biomass conversion and other industries (i.e., paper industry, protein or plant as the production factor for other compounds). For example, excellent utility of crop cultivation may be generated from controlling the size of plant as the overall organs or any parts of the organs, or any number of organs.

Similarly, controlling the size and the height of plant, its specific portion, its rate of growth or seedling vitality enables production of more suitable plants in specific industries. For example, decrease in the height of specific crops and species of trees may be useful according to easier harvesting. Alternatively, the increased height and thickness of the plant, or the size and the number of organs may be made efficient by supplying much more biomass that is useful for processing into food, feed, fuel and/or chemicals. (Refer to the website of United States Department of Energy on energy efficiency and regeneration). Other examples of commercially desirable features include increase in length of the stem of cut flowers, increase or change in the size and shape of leaves, promotion of seeds and/or fruits. Changes in the size and the number of organs, and biomass also lead to change in the weight of components such as the secondary products and conversion into manufacture of compounds which are derived from plant.

Experts and researchers in the fields of Agricultural Science, Agriculture, Crop Science, Gardening, and Forest Science have made continuous efforts to effectively search and produce plants which show increased growth in order to secure the supply of foods and renewable materials to a fast-growing population over the world. In such science fields, their complicated researches point out that they are important leaders in all geographical environments and climates over the world, in supply of sustainable sources of foods, feeds and energy to the group.

Manipulation of performance of agricultural products has been conventionally achieved through plant breeding for centuries. However, such breeding procedure is time-consuming and labor-intensive. Moreover, breeding programs should be specifically designed for relative species of plants.

On the other hand, molecular genetic approaches have been used as an excellent procedure in order to prepare plants that produce better crops. Using introduction and expression of recombinant nucleic acid molecules in the plant, researchers are now prepared for supplying the group with species of plants which are adjusted for more efficient growth and more products, regardless of specific geographical and/or climatic environments. Their new approaches have an additional advantage of applying to other complex species of plants, without being restricted to one species of plant (Zhang et al. (2004) Plant Physiol. 135:615).

Regardless of this procedure, generally applicable procedures are currently required to improve the growth of plants in forest and agricultural industry for the purpose of satisfying specific requests, which depends on specific environmental conditions. Finally, the present invention relates to useful manipulation of the size of plant, the number of organ, the plant's rate of growth, the plant structure and/or biomass in order to make plants grow, seek profits specified by expression of recombinant DNA molecules and maximize profits of various agricultural products which are dependent on a specific environment. These molecules may be originated from the plant itself or simply expressed at a higher or lower level. Moreover, they may be originated from other species of plants.

SUMMARY OF THE INVENTION

Accordingly, the present invention is designed to solve the above-mentioned problems, it is an object of the present invention to provide a protein associated with promotion of plant biomass.

It is another object of the present invention to provide a gene associated with promotion of plant biomass.

It is still another object of the present invention to provide a method for promoting plant biomass using the gene.

It is still another object of the present invention to provide a method for producing a transgenic plant including the gene.

It is yet another object of the present invention to provide the transgenic plant.

According to an aspect of the present invention, there is provided a method for promoting plant biomass by preparation of a small GTP binding protein, RabG3b or mutants of the RabG3b protein and overexpression of genes coding the RabG3b protein or the mutants of the RabG3b protein.

The term "biomass" used in the present invention means a useful biological material including target products, and the material is designed and recovered in additional procedures to separate or concentrate the target products. The term "biomass" may include fruits or their portions, or seeds, leaves, or stems or roots, and they are particularly parts of plants of interest for industrial purpose. As plant materials are mentioned above, the term "biomass" includes any of a structure(s) including or representing the target products.

The term "transformation" used in the present invention includes *Agrobacterium*-mediated transformation [transformation of dicotyledonous plant (Needleman and Wunsch (1970) J. Mol. Biol. 48:443; Pearson and Lipman (1988) Proc. Natl. Acad. Sci. (USA) 85: 2444), transformation of monocotyledonous plant (Yamauchi et al. (1996) Plant Mol. Biol. 30:321-9; Xu et al. (1995) Plant Mol. Biol. 27:237; Yamamoto et al. (1991) Plant Cell 3:371)] and the biolistic method (P. Tijessen, "Hybridization with Nucleic Acid Probes" In Laboratory Techniques in Biochemistry and Molecular Biology, P. C. vand der Vliet, ed., c. 1993 by Elsevier, Amsterdam), electroporation, in planta technology, etc., and examples of means for transformation will be described below. For the plant including exogenous nucleic acids, the first transgenic plant is referred to as $T_0$ and the first generation is referred to as $T_1$ in the present invention.

According to one exemplary embodiment of the present invention, the used RabG3b protein and a gene sequence coding the RabG3b protein are derived from *Arabidopsis thaliana*, and RabG3b gene from other species of interest or pseudo-gene may be also used.

According to another exemplary embodiment, the RabG3b protein preferably has an amino acid sequence set forth in SEQ ID NO: 1, but all mutants, which are obtained by mutation of plants through substitution, deletion and addition of any one or more amino acids in the amino acid sequence set forth in SEQ ID No. 1 and show a desired promotion of biomass in the present invention, are included in the scope of the present invention, and examples of the mutants are mutants having a sequence in which a $67^{th}$ residue is substituted from glutamine to leucine in the amino acid sequence set forth in SEQ ID NO: 1.

However, the gene coding the protein or its mutants preferably have a substantial homology to nucleic acid sequence set forth in SEQ ID NO: 2 or 3, but the present invention is not limited thereto.

In the present invention, the term "substantial homology" of poly nucleotide sequence means a polynucleotide including a sequence showing sequence homology of 60% or higher, normally 70% or higher, and more normally 80% or higher, and most preferably 90% or higher, when a standard parameter is used to compare with a reference sequence in a program described below. Those skilled in the art may recognize that such values may be properly adjusted for measurement of the corresponding identity of a protein encoded by a pair of nucleotide sequences with consideration of codon degeneracy, amino acid similarity and reading frame localization.

An example of algorithm is a BLAST algorithm described in the previous studies (see: Altschul et al., J. Mol. Biol. 215:403-410, 1990), that is suitable for measurement of percentage of sequence homology and similarity. Software for BLAST analysis is available through the web site of National Center for Biotechnology Information (NCBI).

According to another exemplary embodiment, the gene expression is preferably under the control of a promoter.

As the promoter which is suitable for expression while being operationally linked a gene associated with promotion of plant biomass using methods described in the present invention, a promoter originating from the same or different species of transgenic plant may be used. Moreover, the promoter may originate from the same or the different species in aspect to the gene to be used in the present invention. The promoter for use in the present invention may also include a chimera promoter that may include a combination of promoters which have one or more common expression profiles compared to what will be described below.

Methods of determining and characterizing a promoter region in plant genomic DNA have been well known to those skilled in the art. For example, they are described in the previous studies [see: Jordano et al, Plant Cell 1: 855-866, 1989; Bustos et al., Plant Cell 1: 839-854, 1989; Green et al., EMBO J. 7: 4035-4044, 1988; Meier et al., Plant Cell 3: 309-316, 1991; and Zhang et al., Plant Physiol. 110: 1069-1079, 1996].

Examples of this promoter sequence include a promoter for amino acid permease gene (AAP1)(ex: an AAP1 promoter from *Arabidopsis thaliana*) (see: Hirner et al., Plant J. 14: 535-544, 1998), a promoter for an oleate 12-hydroxylase: desaturase gene (ex: a promoter designated as LFAH12 from *Lesquerella fendleri* (see: Broun et al., Plant J. 13: 201-210, 1998), a promoter for a 2S2 albumin gene (ex: a 2S2 promoter from *Arabidopsis thaliana*) (see: Guerche et al., Plant cell 2: 469-478, 1990), a fatty acid elongase gene promoter (FAEI) (ex: FAE1 promoter from *Arabidopsis thaliana*) (see: Rossak et al., Plant Mol. Biol. 46: 717-715, 2001), and a leafy cotyledon gene promoter (LEC2) (ex: a LEC2 promoter from *Arabidopsis thaliana*) (see: Kroj et al Development 130: 6065-6073, 2003).

Moreover, the present invention provides an expression vector for promoting plant biomass comprising a nucleic acid sequence that encodes a RabG3b gene operationally linked to one or more regulatory genes that can promote the expression of plant biomass-related genes.

In the present invention, the term "vector" or "expression vector" generally means a double DNA strand that may be used to insert the vector into exogenous DNA. For example, a vector or a replicon may originate from plasmid or virus. The vector contains "replicon" polynucleotide sequence to promote self-replication of vector in a host cell. Moreover, the term "replicon" used in the art contains a polynucleotide sequence that targets a recombination of a vector sequence into a host chromosome promotes other replications.

Moreover, even when the exogenous DNA may be, for example, inserted into a viral DNA vector in an early stage, transformation of viral vector DNA into the host cell may lead to transcription of viral DNA into viral RNA vector molecules. The exogenous DNA is defined as xenogenic DNA, for example, as DNA that isn't naturally found in the host cell. Here, the DNA serves to replicate and select the vector molecules or encode selectable markers or transgenes. The vector is used to transmit exogenous or xenogenic DNA into a suitable host cell. In the host cell, the vector may replicate independently or differently from host chromosomal DNA, and may form several copies of vectors and DNA inserted into the vectors.

Moreover, the vector may target insertion of exogenous or xenogenic DNA into the host chromosome. The vector, also, may permit transcription of inserted DNA into mRNA molecules, or contain essential elements to induce replication of inserted DNA into a large copy number of RNA. Some expression vectors further include sequence elements which are close to inserted DNA that permits translation of mRNA into protein molecules. Accordingly, polypeptides encoded by many mRNAs and inserted DNA may be promptly synthesized.

The term "transformation vector" used in the present invention means an inserted DNA fragment, in other words, a "transgene" that is inserted into mRNA or replicated as RNA in a host cell.

The term "transgene" in the present invention doesn't mean an inserted DNA fragment to be transcribed into RNA, but means a vector region required for transcription or replication into RNA. Moreover, the transgene doesn't need to essentially contain a polynucleotide sequence comprising open reading frames that may be used to produce proteins.

The terms "transformed host cell," "transformed" and "transformation" in the present invention mean introduction of DNA into a cell. The cell is named as a "host cell," which may be a prokaryotic or eukaryotic cell. One example of representative prokaryotic host cell includes all kinds of *E. coli* strains. One example of representative eukaryotic host cell includes plant cells (ex: Canola, raw cotton, Camelina, Alfalfa, soybean, rice plant, oat, wheat or corn cells), yeast cells, insect cells or animal cells. Generally, introduced DNA is in the form of a vector containing an inserted DNA fragment. A sequence of the introduced DNA may originate from a same or different species of the host cell, or may be a hybrid DNA sequence containing several DNAs and several exogenous DNAs which may originate from the host cell.

In the present invention, the term "plant" includes the overall plants, plant organs (ex: leaves, stems, flowers, roots, etc.), seeds and plant cells (including tissue culture cells) and offspring thereof. In general, a group of plants which may be used in the methods of the present invention are widely varied from a group of higher plants including both monocots and dicots which are applicable to transformation technology to a group of lower plants such as algae. They include all kinds of polyploid plants including polyploidy, diploid and haploid.

The transgenic plant overexpressing RabG3b of the present invention may be, for example, obtained by transfection of a gene transfer vector (ex: plasmid, viral vector, etc.) encoding promoters operationally linked to the RabG3b gene into the plant.

Conventionally, when a vector is plasmid, the vector includes a selectable marker gene, for example, a kanamycin gene encoding tolerance to kanamycin. The most general method for transformation of a plant includes: cloning a target transgene into a plant transformation vector, and transforming the plant transformation vector into *Agrobacterium tumifaciens* including a helper Ti-plasmid, as described in the previous studies [see: Hoeckeme et al., Nature 303: 179-181, 1983]. For example, an additional method is described in the previous studies (see: Maloney et al., Plant Cell Reports 8: 238, 1989). *Agrobacterium* cell containing the transformation vector may be cultivated with leaf lobes of the plant to be transformed, as described in the previous studies (see: An et al., Plant Physiol. 81: 301-305, 1986; Hooykaas, Plant Mol. Biol. 13: 327-336, 1989). As conventionally described above, the transformation of cultivated plant host cell may be achieved using *Agrobacterium tumefaciens*. In general, a culture extract of the host cell that does not have a solid cell membrane barrier is originally described in the previous studies (see: Graham et al., Virology 52: 546, 1978) and transformed using a transformed calcium phosphate method, as described in the previous studies (see: Sambrook et al., Molecular Cloning: A Laboratory Manual (2nd Ed., 1989 Cold Spring Harbor Laboratory Press, New York, N.Y.). However, another method for introducing DNA into cells may also be used, which includes a polybrene test (see: Kawai et al., Mol. Cell. Biol. 4: 1172, 1984), a protoplast fusion (see: Schaffner, Proc. Natl. Acad. Sci. USA 77: 2163, 1980), electroporation (see: Neumann et al., EMBO J. 1: 841, 1982) and direct microinjection into the nucleus (see: Capecchi, Cell 22: 479, 1980). Transformed plant cells may be, for example, selected with a selectable marker by cultivating cells on medium containing a phytohormone such as kanamycine, naphthalene acetic acid and benzyladenine, which are used to induce formation of callus and shoots. Afterwards, plants obtained by regeneration of the plant cells may be transferred to the soil using technologies widely known to those skilled in the art.

In addition to the above-mentioned methods, a large number of methods are widely known in the art, which includes transferring the cloned DNA into various species of the plants including gymnosperm, sporic plant, monocot and dicot [see: Glick and Thompson, eds., Methods in Plant Molecular Biology and Biotechnology, CRC Press, Boca Raton, Fla., 1993; Vasil, Plant Mol. Biol, 25: 925-937, 1994; and Komai et al., Current Opinions Plant Biol. 1: 161-165, 1998 (general review); Loopstra et al., Plant Mol. Biol. 15: 1-9, 1990; and Brasileiro et al., Plant Mol. Biol. 17: 441-452, 1990 (tree transformation); Eimert et al., Plant Mol. Biol. 19: 485-490, 1992 (*brassica* transformation); Hiei et al., Plant J. 6: 271-282, 1994; Hiei et al., Plant Mol. Biol. 35: 205-218, 1997; Chan et al., Plant Mol. Biol. 22: 491-506, 1993; U.S. Pat. Nos. 5,516,668 and 5,824,857 (rice plant transformation); and U.S. Pat. No. 5,955,362 (wheat transformation); U.S. Pat. No. 5,969,213 (monocot transformation); U.S. Pat. No. 5,780,798 (corn transformation); U.S. Pat. No. 5,959,179 and U.S. Pat. No. 5,914,451 (soybean transformation)].

Representative examples include protoplast electroporation-accelerated DNA absorption (see: Rhodes et al., Science 240: 204-207, 1988; Bates, Meth. Mol. Biol. 111: 359-366, 1999; DHalluin et al., Meth. Mol. Biol. 111: 367-373, 1999; U.S. Pat. No. 5,914,451); protoplast treatment using polyethylene glycol (see: Lyznik et al., Plant Mol. Biol. 13: 151-161, 1989; Datta et al., Meth. Mol. Biol., 111: 335-334, 1999); and bombardment of cells using microprojection containing DNA (see: Klein et al., Plant Physiol. 91: 440-444, 1989; Boynton et al., Science 240: 1534-1538, 1988; Register et al., Plant Mol. Biol. 25: 951-961, 1994; Barcelo et al., Plant J. 5: 583-592, 1994; Vasil et al., Meth. Mol. Biol. 111: 349-358, 1999; Christou, Plant Mol. Biol. 35: 197-203, 1997; Finer et al., Curr. Top. Microbiol. Immunol. 240: 59-80, 1999). In addition, plant transformation steps and technologies are found in the previous studies (see: Birch, Ann. Rev. Plant Phys. Plant Mol. Biol. 48: 297, 1997; Forester et al., Exp. Agric. 33: 15-33, 1997). Their slight variation enables the technologies in the art to be applicable to wide-ranging species of the plants.

For transformation of monocots, particle bombardment is a conventional selection method. However, monocots such as corn may be also transformed using *Agrobacterium* transformation method as described in U.S. Pat. No. 5,591,616.

Another method for transformation of monocots such as corn includes, for example, mixing cells from an embryonic suspension culture with a fiber suspension [5% w/v, Silar SC-9 whiskers] and plasmid DNA (1 μg/μl) and horizontally keeping the cells in a large number of sample heads in a Vortex GENIE II vortex mixer [manufactured by Scientific Industries, Inc., located in Bohemia, N.Y., U.S.] or in a holder of a MIXOMAT dental amalgam mixer [manufactured by Degussa Canada Ltd., located in Ontario, Burlington, Canada]. Then, transformation may be performed by mixing for approximately 60 seconds (for example, using Vortex GENIE II) at the highest speed or shaking at a regular speed for 1 second (MIXOMAT). According to the process of the present invention, a group of cells from which stable transformants may be screened are produced. Then, the southern hybrid analysis may be used to regenerate plants from stably transformed callus and transform the plants and their offspring.

For example, U.S. Pat. No. 5,464,765 discloses the use of plants cells, particularly corn silk for corn transformation. U.S. Pat. No. 5,968,830 discloses a method for transforming and regenerating soy beans. Moreover, U.S. Pat. No. 5,969,215 discloses a transformation technology for producing a transformed *Beta vulgaris* plant as sugar beet.

The above-mentioned transformation technologies have their advantages and disadvantages. In each technology, genetic manipulation of DNA from plasmid makes it possible to contain a selectable and screenable marker gene as well as a target gene. The screenable marker gene may be used to select only cells with integrated copies of plasmid (a construct of the present invention is used to transform a target gene and a screenable gene as units). Such screenable gene provides other inspections for successful cultivation of cells with the target gene only.

Conventional *Agrobacterium* transformation using a screenable marker of antibiotic resistance may be problematic since these transformed plants may have high risk in spreading antibiotic resistance to animals and human beings. Such antibiotic marker may be removed from plants by producing a transformed plant using the *Agrobacterium* technology similar to the technology is described in U.S. Pat. No. 5,731,179. The antibiotic resistance-related problems may be effectively avoided using a bar or pat encoding sequence, as described in U.S. Pat. No. 5,712,135. Such desirable marker DNA encodes a secondary protein or polypeptide that suppresses or neutralizes actions of a glutamine synthetase inhibitor, a weed-killer, phosphinothricin (Glufosinate) and Glufosinate-ammonium salt (Basta, Ignite).

Plasmid containing at least one of these genes is introduced into plant protoplast or callus using one of the technologies described above. When the marker gene is a screenable gene, only cells including a DNA package survive under the screening conditions using a proper plant toxin. When proper cells are screened and grown, their plants are regenerated. It is confirmed that the DNA package is successfully integrated into plant genome by testing the offspring from the transformed plants.

There are a large number of factors that affect the success of transformation. Components for designing, constructing and controlling an exogenic gene construct may affect integration of an exogenic sequence chromosomal DNA of the plant nucleus and an ability of a transgene to be expressed by cells. It is essential to introduce the exogenic gene construct into the plant nucleus using a non-toxic method. It is important to provide a proper regeneration protocol because a cell type into which the construct is introduced may be adjusted for regeneration when the overall plants are recovered.

Moreover, a prokaryotic cell may be used as a host cell at an initial cloning stage according to the present invention. Methods, vectors, plasmid and host cell systems are well known to those skilled in the art, which may be used at such initial cloning and expansion stages and will not be described in the present invention.

According to another exemplary embodiment of the present invention, a promoter may be operationally linked to genes that may encode plant biomass promotion-related genes such as RabG3b in plants to be transformed using methods widely known to those skilled in the art. Insertion of the promoter leads to gene expression in developing seeds of transgenic plants.

In the method of the present invention, the transgenic plant includes monocots and dicots, but the present invention is not limited thereto. Among them, plants of interest include Canola, raw cotton, wheat, rice plant, soybean, barley and other seed-producing plants, and Alfalfa. Also, the plants of interest includes, but is not limited to, other plants, and all agricultural, commercial and other industrial plants of interest.

The term "xenogeneic sequence" used in the present invention means an oligonucleotide sequence that is substantially modified from its original type, when such sequence originates from the different or same species. For example, a xenogeneic promoter operationally linked to a structural gene originates from a species different from that of the structural gene, or originates from a species that is substantially modified from its original type when the sequence originates from the same species.

The term "primer" used in the present invention is a separated nucleic acid that annealed with a complementary target DNA strand through nucleic acid hybridization, thus forming a hybrid between the primer and target DNA strand, and then is extended along the target DNA strand by means of polymerase, for example, DNA polymerase. A pair of primers according to the present invention may be used to amplify a target nucleic acid sequence using polymerase chain reaction (PCR) or other conventional nucleic acid amplification methods.

Methods for preparing and using probes and primers are, for examples, described in the studies (Molecular Cloning: A Laboratory Manual, 2nd ed., vol. 1-3, ed. Sambrook et al., Cold Spring Harbor Laboratory Press, Cold Spring Harbor, N.Y., 1989 (hereinafter, "Sambrook et al., 1989"); Current Protocols in Molecular Biology, ed. Ausubel et al., Greene Publishing and Wiley-Interscience, New York, 1992 (periodically revised) (hereinafter, "Ausubel et al., 1992"); and Innis et al., PCR Protocols: A Guide to Methods and Applications, Academic Press: San Diego, 1990). Pairs of PCR primers may be, for example, derived from known sequences using a computer programs such as Primer (Version 0.5, © 1991, Whitehead Institute for Biomedical Research, Cambridge, Mass.) developed for this purpose.

For the nucleic acid amplification, any of various nucleic acid amplification methods including PCR as known in the art may be used. Various amplification methods are known to those skilled in the art, and particularly described in U.S. Pat. No. 4,683,195 and U.S. Pat. No. 4,683,202, and PCR Protocols: A Guide to Methods and Applications, ed. Innis et al., Academic Press, San Diego, 1990. PCR amplification methods have been advanced to amplify genomic DNA of maximum 22 kb and bacteriophage DNA of maximum 42 kb (Cheng et al., Proc. Natl. Acad. Sci. USA 91: 5695-5699, 1994).

Hereinafter, the present invention will be described.

A tracheary element (hereinafter, referred to as 'TE') of xylem serves as xylem for transporting water in the vascular system. For this, TE proceeds into secondary cell wall thickening and cell death. The cell death of TE is typical embryologically programmed cell death by autophagy. However, there is no known evidence about the autophagy in TE differentiation. The present invention has found that a small GTP binding protein, RabG3b, participates in the TE differentiation through action of the autophagy. It was found that the differentiation of wild-type TE cells undergo the autophagy in an *Arabidopsis* culture system. Both of the autophagy and TE differentiation are remarkably accelerated by continuous overexpression of an activated mutant (RabG3bCA) and suppressed in transformed plants overexpressing a dominant-negative mutant (RabG3bDN) or RabG3b RNAi, a brassinosteroid insensitive mutant bri1-301, and an autophagy mutant atg5-1. Based on these results, the present invention suggests that the autophagy occurs during the TE differentiation, and RabG3b as a component of the autophagy serves to control the TE differentiation.

The cell death occurring in the last stage of development of xylem, particularly, differentiation of duct cells is a very important procedure for completion of xylem. Because all contents of protoplasm are disintegrated during this procedure to form hollow xylem. According to the present invention, it is confirmed that autophagy accelerates the cell death in such xylem development. Finally, when RabG3bCA in a constitutively active type of RabG3b participating in the autophagy is overexpressed, the autophagy is accelerated during the xylem development, which leads to accelerated cell death, thus promoting development of xylem in the plant stem.

The importance of the present invention is as follows.

Xylem is a tissue that forms a wood layer in plants. Accordingly, when the same characters (i.e., increase of xylem) as observed from Arabidopsis thaliana are formed by overexpressing overexpressed RabG3bCA according to the present invention in plants, these characters are very important since they are applicable in industries. This is because it means promotion of plant biomass. For now, trees such as poplar or eucalyptus are used as a representative wood material. Wood is the main material for pulp and paper. Moreover, it has come into the spotlight as an important material of production of bioethanol (next-generation alternative energy), which is one of the current hot issues.

Hereinafter, the present invention will be described in more detail.

RabG3b Functions for Xylem Differentiation.

The small GTP binding protein RabG3b was identified as a salicylic acid reaction protein by proteomic analysis (Oh et al., 2005). Microarray analysis showed that RabG3b is highly expressed in response to brassinolide (BL)/$H_3BO_3$ treatment (FIG. 12).

The present invention examined (1) whether RabG3b participates in TE differentiation, (2) whether RabG3b participates in autophagy and (3) whether autophagy participates in TE differentiation.

RabG3b knockdown plant (RabG3bRNAi) was produced, in which RabG3b expression was reduced among a member of tested RabG3 family, and RabG3b proteins were not significantly detected by Western Blot Analysis (FIG. 13). Two different RabG3b transgenic plants, RabG3bCA and RabG3bDN representing a continuously active (CA) and dominant-negative (DN) mutant RabG3b, respectively, are also used in characteristics analysis. Moreover, a BR-insensitive mutant bri1-301 including vascular deletion (Cano-Delgado, A., et al. (2004) *Development*, 131, 5341-5351) and autophagy mutant atg5-1 (Thompson, A. R., et al. (2005) *Plant Physiol.* 138, 2097-2110) were used.

Growth phenotypes of plants were investigated under long-day conditions (16/8 h light/dark cycle) (FIG. 1). As a dominant phenotype, a RabG3bCA plant has a stem growing more highly than other tested plants, and stem thickening increased by approximately 14%, compared to the WT plant (FIGS. 1b and c). In contrast, it was shown that an atg5-1 plant was grown in length shorter than the WT plant, and a bri1-301 plant is severely reduced in size. For bolting, the number and bolting time of rosette leafs were determined. RabG3bCA plant has been bolted earlier than the other plants (FIG. 14), but there was no considerable difference in the number of leafs from tested plants (FIG. 15). These results show that the increased length of stem in the RabG3bCA plant is due to faster stem growth, rather than adjustment of blooming time.

Then, the possible relationship between changes in vascular development and growth phenotypes was investigated through histological analysis of cross sections of inflorescence stems which are derived from three different positions of plants (FIGS. 2 and 3). All the vascular phenotypes of plants appeared normal, whereas the number of xylem cells considerably increased in the middle and the basal regions of the RabG3bCA inflorescence stems, in comparison with the WT plant (FIG. 2). Moreover, quantification of xylem cells, which are divided into two different types of metaxylem and protoxylem, indicated that the number of metaxylem cells was remarkably increased in vascular bundles of the RabG3bCA plant, compared to the WT plant (FIGS. 3, 4, and 16).

In contrast, the RabG3bDN, RabG3bRNAi, and atg5-1 plants showed a significant decrease in number of both protoxylem and metaxylem in the basal region of inflorescence stems. These results show that the increased stem growth is associated with increased xylem differentiation in the RabG3bCA plant. Moreover, a decrease in number of xylem cells in the atg5-1 plant suggests that ATG5 and ATG5-linked autophagy may be associated with xylem differentiation.

Formation of a secondary cell wall that is an index of the xylem differentiation was examined in a cross section of the inflorescence stem using lignin staining (FIG. 17 a-f) with phloroglucinol-HCl and lignin autofluorescence (FIG. 17 g-l).

Lignified cell walls are expanded in the RabG3bCA plant, in comparison with the WT plant, whereas they are somewhat decreased in thickness in the RabG3bDN, RabG3bRNAi, bri1-301, and atg5-1 plants.

Localization of RabG3b in the inflorescence stems was investigated through immunogold electron microscopy using anti-RabG3b antibody (FIG. 18). RabG3b protein was largely located in xylem. In a cortex cell, gold particles were found in several sites including protoplasm, vacuole and cell wall (FIG. 18e-h), but in a xylem TE cell deficient in protoplasm contents, RabG3b immunity was observed only in the secondary cell wall (FIG. 18m-p).

TE Formation Increases in RabG3bCA-Cultured Cells During Xylem Differentiation.

In order to define functions of RabG3b in the xylem differentiation, an in vitro xylem TE inducible system was developed to culture *Arabidopsis*-suspended cells. When the TE differentiation was induced by BL and $H_3BO_3$ treatment, RabG3bCA cells largely underwent vacuole rupture and loss of cell contents 4 days after the TE induction (FIG. 19). Then, in comparison with the WT plant, RabG3bCA cells were considerably more generated into TE (FIG. 5). In contrast, few cells differentiated from TE-induced culture of RabG3bDN, RabG3bRNAi, atg5-1, and bri1-301 are not observed, compared to the WT plant. Robust lignin staining was additionally observed in the RabG3bCA cells (FIG. 20). These results suggest that RabG3b plays a positive role in the TE differentiation and ATG5-mediated autophagy has a positive effect on the TE differentiation.

Autophagy is Activated During TE Differentiation.

In order to determine whether RabG3b regulates the TE differentiation in the autophagy using its functions, an autophagy procedure was examined during TE formation by staining autophagic vacuole/lysosome with an acidotropic dye such as LysoTracker Green (LTG) (Via, L. E., et al. (1998) *J. Cell Sci.* 111, 897-905) (FIG. 6). Prior to TE induction, LTG-stained structures were not detected in the tested plants, except for the RabG3bCA cells showing some faintly stained spots (FIG. 6a-e). BL and $H_3BO_3$ treatment induced the formation of LTG-stained autophagic vacuole/lysosome-like structures in WT cells, and this structure is remarkably increased in the RabG3bCA cells (FIG. 6k-l). Under the same inducing conditions, no LTG-stained structures were formed in the RabG3bDN, RabG3bRNAi, or atg5-1 cells (FIG. 6c-e, h-j and m-o). From these results, it was revealed that the autophagy may occur during the TE differentiation, and be activated by GTP-binding of RabG3b.

RabG3bCA Cells Have Many Autophagic Structures Accumulated During TE Differentiation.

Transmission electron microscope (TEM) analysis was conducted during the TE differentiation in order to examine microstructural changes in cells and determine LTG staining results (FIG. 7). Non-induced cells showed fewer morphological differences in the tested plants (FIG. 7a-e). For the TE induction, disintegration of cell contents and vacuole rupture were observed in the WT cells 4 days after the BL/H$_3$BO$_3$ treatment (FIG. 7f). During this period, the WT cells show autophagic vacuole/lysosome-like structure including disintegrated cell components (FIGS. 7f and p). A large number of autophagic vacuole/lysosome-like structures are accumulated in the RabG3bCA cells, resulting in rapid loss of cell organs and contents (FIGS. 7g and q). After 7 days of the TE induction, the RabG3bCA cells were completely differentiated into mature TE cells. This is confirmed by accumulation of hollow protoplast and secondary cell walls (FIG. 7l). Moreover, the WT cells have still proceeded into the last stage of the TE differentiation (FIG. 7k). In contrast, no autophagic vacuole/lysosome-like structures and TE-related morphological changes were observed in the RabG3bDN, RabG3bRNAi, or atg5-1 cells during the TE inducement (FIG. 7h-j and m-o).

During the TE differentiation, the formation of autophagic structures was further investigated in the WT and RabG3bCA cells (FIG. 8a-h). The WT cells showed preautophagosomal structures or phagophores (FIG. 8b), and accompanied autophagic vacuole/lysosome-like structures (FIGS. 8c and d). Although the similar autophagic structures were observed in the RabG3bCA cells, they were formed earlier cells and more affluent, compared to the WT cells (FIG. 8e-h). A large number of phagophores including protoplast materials and cell organelles (i.e., mitochondria) were observed after 1 day of the BL/H$_3$BO$_3$ treatment (FIG. 8e), and accumulation of the autophagic vacuoles was observed in the treated RabG3bCA cells after 2 days. Moreover, the preautophagosomal structures is still expanded in the WT cells. Then, the present inventors further tested whether activation of autophagy in the RabG3bCA cells is observed under the nutrient deficiency as a general autophagy condition (FIG. 8i-p). Similarly, both of the WT and RabG3bCA cells showed autophagic structures in response to sucrose starvation, and the autophagic structures are shown earlier cells and more affluent in the RabG3bCA cells, compared to the WT cells. Such results suggest that the RabG3b is a positive regulator for autophagy and RabG3b-activated autophagy induces the cell death, thus contributing to the TE differentiation.

RabG3b is Localized in Autophagic Structures.

For autophagic vacuole/lysosome structures, localization of RabG3b proteins was analyzed through immunogold EM using antisera against the autophagic vacuole marker protein ATG8e and RabG3b in the TE-induced WT and RabG3bCA cells. In both of the WT and RabG3bCA cells, the RabG3b proteins were co-localized with the ATG8e protein in the autophagic structures (FIG. 9a-d). Moreover, a level of the ATG8e protein was increased in the RabG3bCA cells, compared to the WT cells, and mostly was associated with autophagic structures and more increased in the BL/H$_3$BO$_3$-treated RabG3bCA cells (FIG. 9e).

Expression Analysis of Autophagy- and Xylem Differentiation-Related Genes

According to the microarray data using Genevestigator, more than 20 of 36 currently defined autophagy-related genes (ATGs) are up-regulated during PCD or BL/H$_3$BO$_3$ treatment. Therefore, 13 ATG genes implicated in several stages of the autophagy were selected and their expression levels were examined during the TE differentiation. Among the tested ATG genes, 9 genes showed no remarkable increase (less than 2 times), but 4 ATG genes (ATG6, 8g, 18h, and VPS34) were up-regulated more than 2 times in the BL/H$_3$BO$_3$ treatment. Such results support that the autophagy is associated with the TE differentiation (FIG. 10a). Moreover, in the late stage of the TE differentiation, expression levels of specific two groups of genes were investigated: PCD-related gene (BFN1, XCP1, AtXyn3, and AtMC9) and secondary cell wall-related gene (IRX1, 3, 5, 12, FRA8, CcOAOMT, and 4CL1) (FIGS. 21 and 22). Expression of vascular system-related transcription factor genes (AtHB8, AtHB15, PHB, PHV, REV, VND6, and VND7), which control the initial stage of the TE differentiation, were examined, as well as BR-related genes (BRI1, BRL1, 2, and 3) (FIGS. 23a and 24a). A large number of the tested genes were greatly increased in transcriptome level in response to the TE induction.

Expression of the up-regulated ATGs (ATG 6, 8g, 18h, and VPS34) was compared to the WT, RabG3bCA, and atg5-1 cells during the TE induction, but there are no differences in expression of several cell strains (FIG. 10b). Since a great increase in the ATG8e proteins was already observed in both of the untreated and BL/H$_3$BO$_3$-treated RabG3bCA cells (FIG. 9e), the ATG8e expression was additionally determined in the WT, RabG3bCA, and atg5-1 cells (FIG. 25). The level of ATG8e basal transcriptome showed higher in RabG3bCA cells, in comparison with WT cells.

Expression of up-regulated PCD-related (AtMC9, XCP1, and BFN1), secondary cell wall-related (IRX1, 5, 12 and FRA8), vascular system-related transcription factors (AtHB8, REV, and VND7), and BR-related (BRL2 and BRL3) genes was examined in WT, RabG3bCA, and atg5-1 cells. The tested PCD- and secondary cell wall-related genes were more strongly expressed in the RabG3bCA cells during the TE differentiation, compared to the WT cells (FIG. 11), which suggests that the PCD and secondary cell wall accumulation is up-regulated in the RabG3bCA cells.

The expression of the vascular system-related transcription factors and BR-related genes showed no considerable difference in the tested cells (FIGS. 23b and 24b). Such results indicate that the functions of RabG3b are more important after TE differentiation than during the initial vascular development.

BRIEF DESCRIPTION OF THE DRAWINGS

The patent or application file contains at least one drawing executed in color. Copies of this patent or patent application publication with color drawings will be provided by the Office upon request and payment of the necessary fee.

The above and other aspects, features and other advantages of the present invention will be more clearly understood from the following detailed description taken in conjunction with the accompanying drawings, in which:

FIG. 1 is a diagram illustrating phenotypes of WT, RabG3bCA, RabG3bDN, RabG3bRNAi, atg5-1, and bri1-301 plants:

(a) Growth phenotypes of WT, RabG3bCA, RabG3bDN, RabG3bRNAi, atg5-1, and bri1-301 plants. 6-week old plants are photographed.

(b) Stem length of plants in (a). Asterisks denote significant differences from the WT. (t Test: *P<0.05; **P<0.01; n=10). This experiment is repeated three with similar results.

(c) Stem thickness measured in a lower-end portion of inflorescence stem of the plant in (a).

Asterisks denote significant differences from the WT. (t Test; *P<0.05; **P<0.01; n=10). This experiment is repeated three with similar results.

Figure 2:
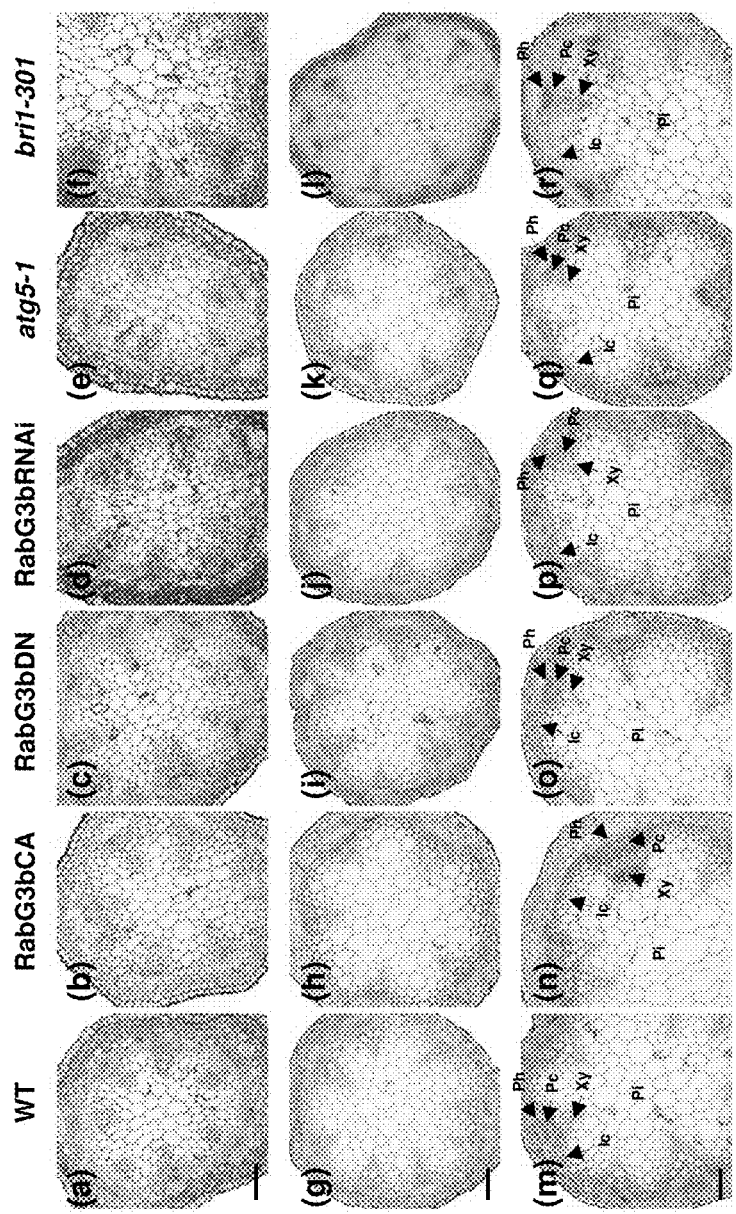

FIG. 2 is a diagram illustrating vascular bundles of inflorescence stems developed in WT, RabG3bCA, RabG3bDN, RabG3bRNAi, atg5-1, and bri1-301 plants.

(a-r) Resin-filled cross sections of end (a-f), middle (g-l) and basal (m-r) regions of the inflorescence stems of the WT, RabG3bCA (#4-2), RabG3bDN (#2-11), RabG3bRNAi (#1-2), atg5-1, and bri1-301 plants, which are 6-week-old, stained with Toluidine blue.

Ic, interfascicular cambium; Pc, (pro) cambium; Ph, phloem; Xy, xylem; Pi, pith.

Bar=50 µm in (a-f), 100 µm in (g-r).

Figure 3:
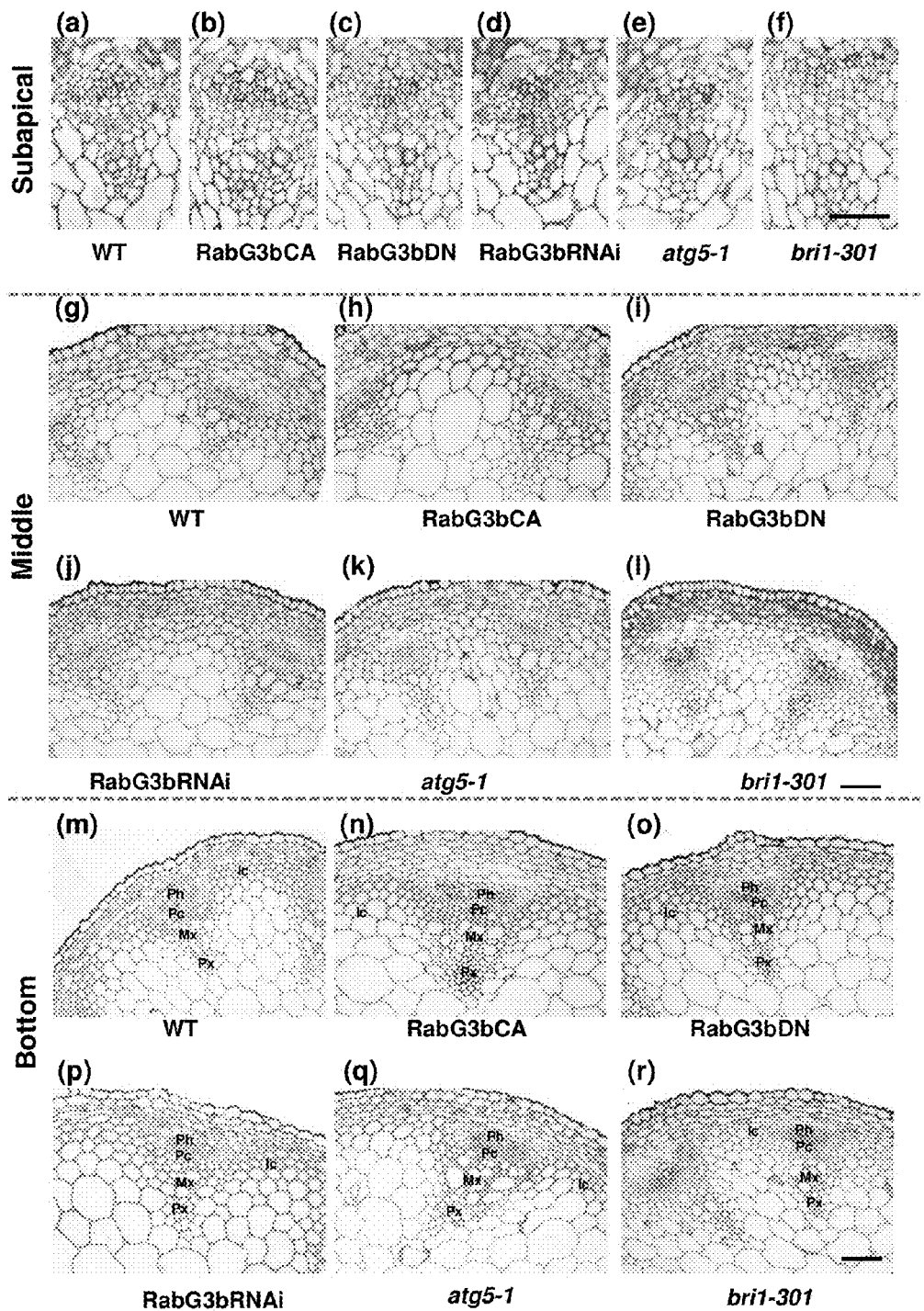

FIG. 3 is a diagram illustrating vascular patterns of inflorescence stems in WT, RabG3bCA, RabG3bDN, RabG3bRNAi, atg5-1, and bri1-301 plants.

(a-r) Resin-filled cross sections of end (a-f), middle (g-l) and basal (m-r) regions of the inflorescence stems of the WT, RabG3bCA (#4-2), RabG3bDN (#2-11), RabG3bRNAi (#1-2), atg5-1, and bri1-301 plants, which are 6-week-old, stained with Toluidine blue.

Ic, interfascicular cambium; Pc, (pro) cambium; Ph, phloem; Mx, metaxylem; Px, protoxylem; Pi, pith.

Bar=20 µm in (a-f), 50 µm in (g-r)

Figure 4:
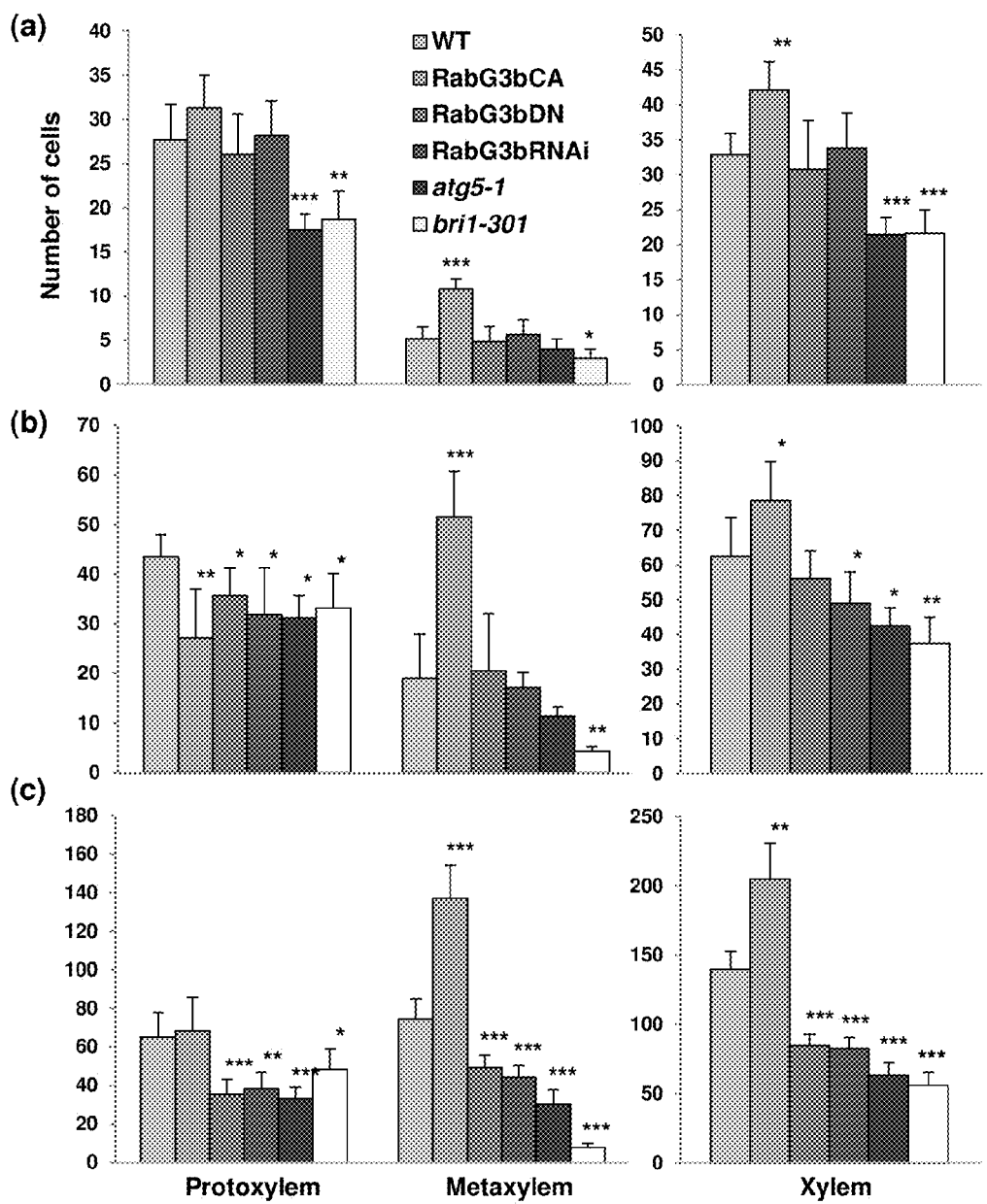

FIG. 4 is a diagram illustrating quantitative analysis of xylem cells in WT, RabG3bCA, RabG3bDN, RabG3bRNAi, atg5-1, and bri1-301 plants.

(a-c) Quantification of the number of protoxylem and metalxylem cells, and the number of xylem cells bound thereto in end (a), middle (b) and basal (c) regions of inflorescence stems of the WT, RabG3bCA (#4-2), RabG3bDN (#2-11), RabG3bRNAi (#1-2), atg5-1, and bri1-301 plants, which are 6-week old.

Asterisks denote significant differences from each WT cells (t Test; *P<0.05; P<0.01;*P<0.001; n=10).

Figure 5:
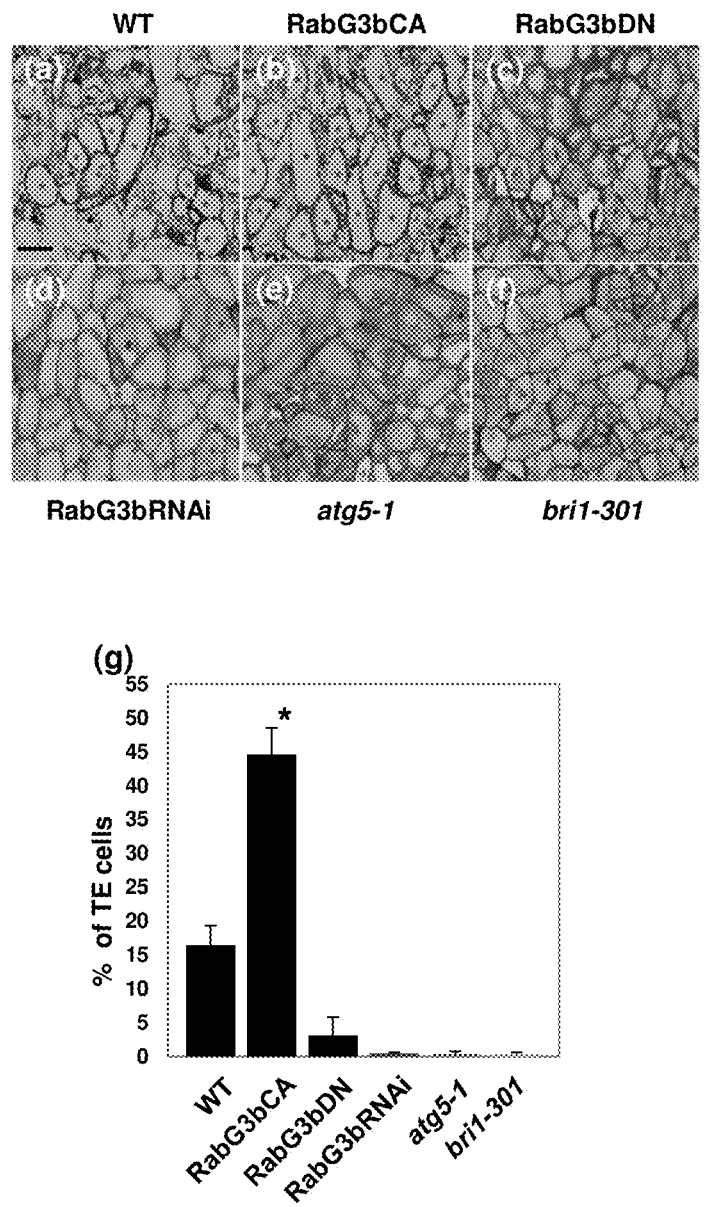

FIG. 5 is a diagram illustrating TE differentiation of cells cultured in WT, RabG3bCA, RabG3bDN, RabG3bRNAi, atg5-1, and bri1-301 plants.

(a-f) Microscopic images of cultured cells for the TE-differentiation. Mature TEs having specific patterns of secondary cell walls are represented as the asterisk. Bar=10 µm.

(g) Quantitative analysis of TE formation. In (a-f), Toluidine blue-stained cultured cells are photographed and mature TEs are counted in the area of 200 µm² in which 300-500 cells are present.

The results are represented by means±SE of three independent experiments. Asterisks denote significant differences from the WT (t test; *P<0.01).

Figure 6:
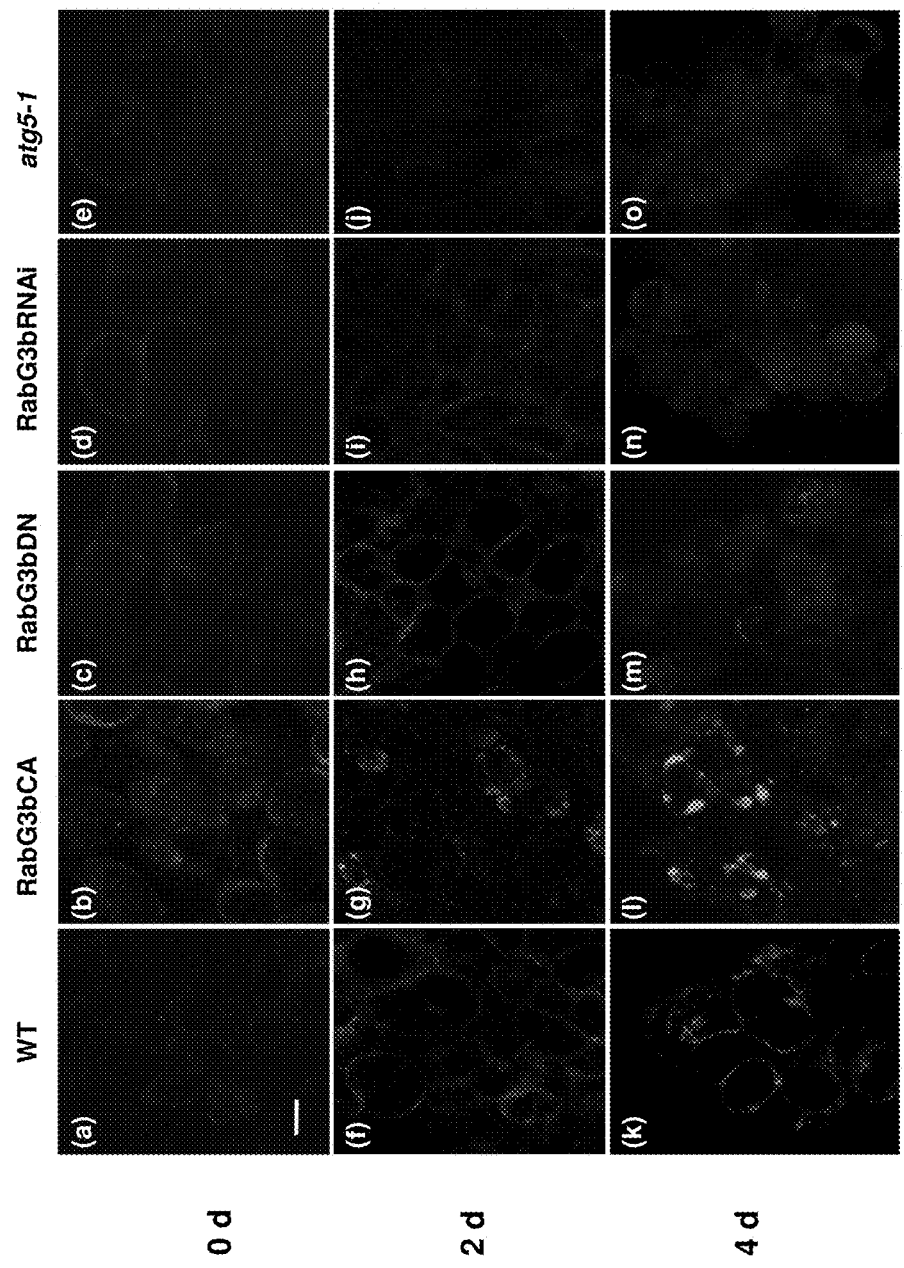

FIG. 6 is a diagram illustrating autophagy activation in culture cells in which TEs are being differentiated.

(a-o) LTG staining of autophagic structures in cells cultured from WT, RabG3bCA (#4-2), RabG3bDN (#2-11), RabG3bRNAi (#1-2), atg5-1, and bri1-301 plants. After 0 (a-e), 2 (f-j), and 4 (k-o) days of BL/H$_3$BO$_3$ treatment, cultured cells are stained with LGT. Green spots represent autophagic vacuole/lysosome structures.

Bar=10 µm.

Figure 7:
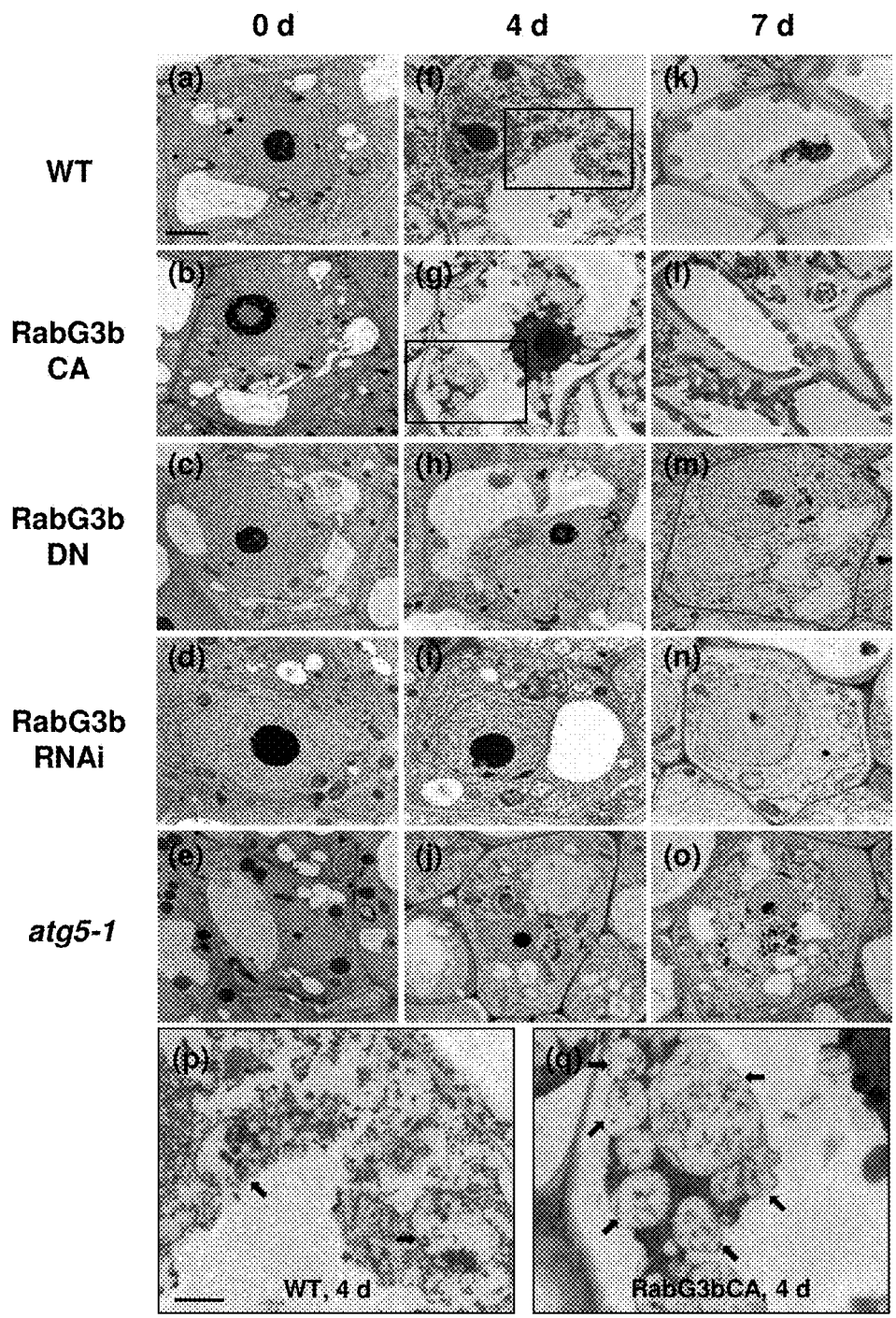

FIG. 7 is a diagram illustrating TEM images of autophagic structures in culture cells in which TEs are being differentiated.

(a-o) LTG staining of autophagic structures in cells cultured from WT, RabG3bCA (#4-2), RabG3bDN (#2-11), RabG3bRNAi (#1-2), atg5-1, and bri1-301 plants. After 0 (a-e), 2 (f-j), and 4 (k-o) days of BL/H$_3$BO$_3$ treatment, cultured cells are stained with LGT. Green spots represent autophagic vacuole/lysosome structures.

(p, q) images in boxes in (f) and (g) are enlarged in (p) and (q), respectively.

Autophagic vacuole/lysosome-like structures are represented by the arrows.

Bar=2 µm in (a-o) and 0.1 µm in (p,q)

Figure 8:
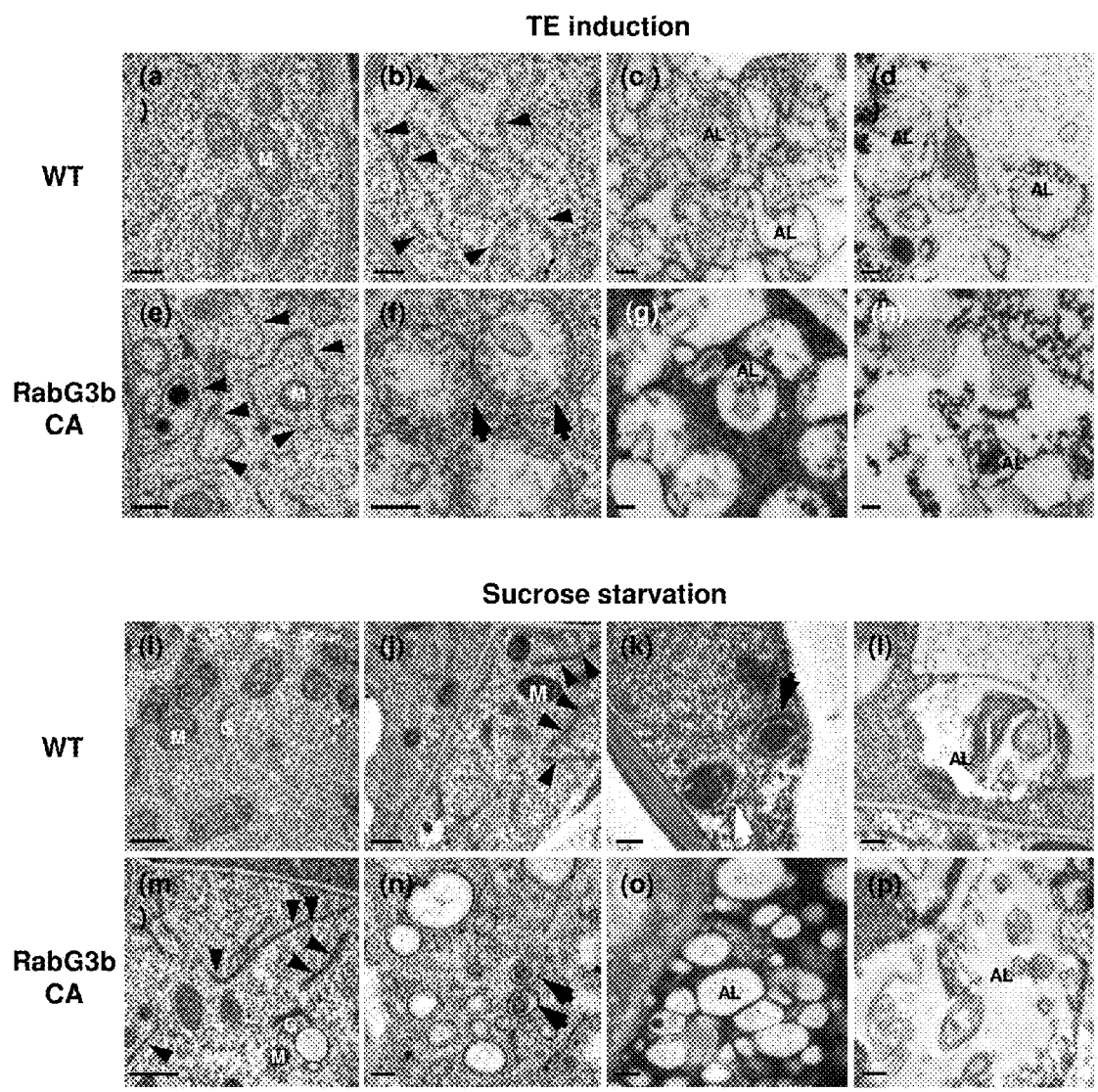

FIG. 8 is a diagram illustrating TEM images of autophagic structures in WT and RabG3bCA cells during TE differentiation and in response to sucrose starvation.

(a-d) Effects of TE induction on formation of autophagic structures in WT cell.

Collection of TEM images of protoplast of WT culture cells which are BL/H$_3$BO$_3$ treated for 1 (a), 2 (b), and 4 (c,d) days (e-h) Effects of TE induction on formation of autophagic structures in RabG3bCA cells Collection of TEM images of protoplast of RabG3bCA culture cells which are BL/H$_3$BO$_3$-treated for 1 (e), 2 (f), and 4 (g,h) days (i-l) Effect of sucrose starvation on formation of autophagic structures in WT cell After 0 (i), 1 (j), and 2 (k,l) days of the sucrose starvation, collection of TEM images of protoplast of WT seedling (m-p) Effect of sucrose starvation on formation of autophagic structures in RabG3bCA cell After 0 (m), 1 (n), and 2 (o,p) days of the sucrose starvation, collection of TEM images of protoplast of RabG3bCA seedling M: Mitochondria; G: Golgi body; AL: Autophagic vacuole/lysosome-like structure; Arrow head: preautophagosomal structure/phagophore; Arrow: autophagosome. Bar=0.5 µm.

Figure 9:
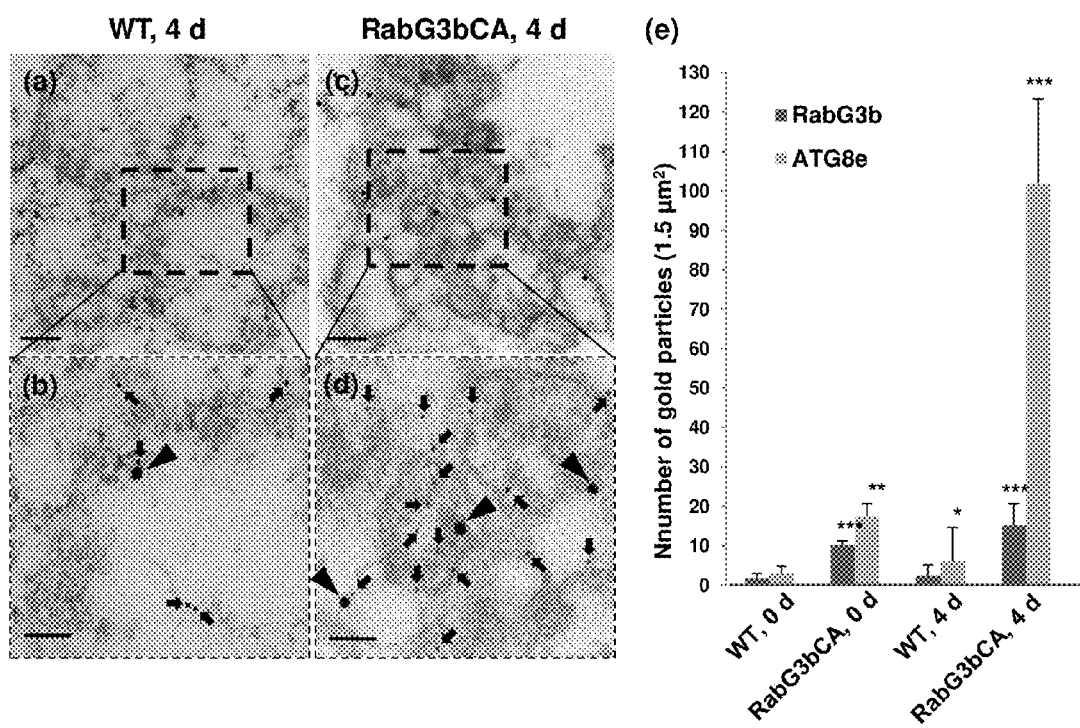

FIG. 9 is a diagram illustrating co-localization of RabG3b and ATG8e in the autophagic structures.

(a-d) Immunogold labeling for co-localization of RabG3b and ATG8e in culture cells treated with BL/H$_3$BO$_3$ for 4 days. The arrow head and the arrow represent RabG3b (20-nm gold) and ATG8e (1-nm gold), respectively. Images in boxes in (a) and (c) are enlarged in (b) and (d), respectively.

Bar=0.2 µm in (a, c) and 0.1 µm in (b, d)

(e) Quantitative analysis of RabG3b and ATG8e proteins in WT and RabG3bCA culture cells which are untreated or treated with WBL/H$_3$BO$_3$ for 4 days. RabG3b and ATG8e gold particles are counted in the area of 1.5 µm² of the TEM image, as shown in (b) and (d). The results are represented by means±SE of six independent experiments.

Asterisks denote significant differences from each WT cell (t test; *P<0.05; P<0.01;*P<0.001; n=10).

Figure 10:
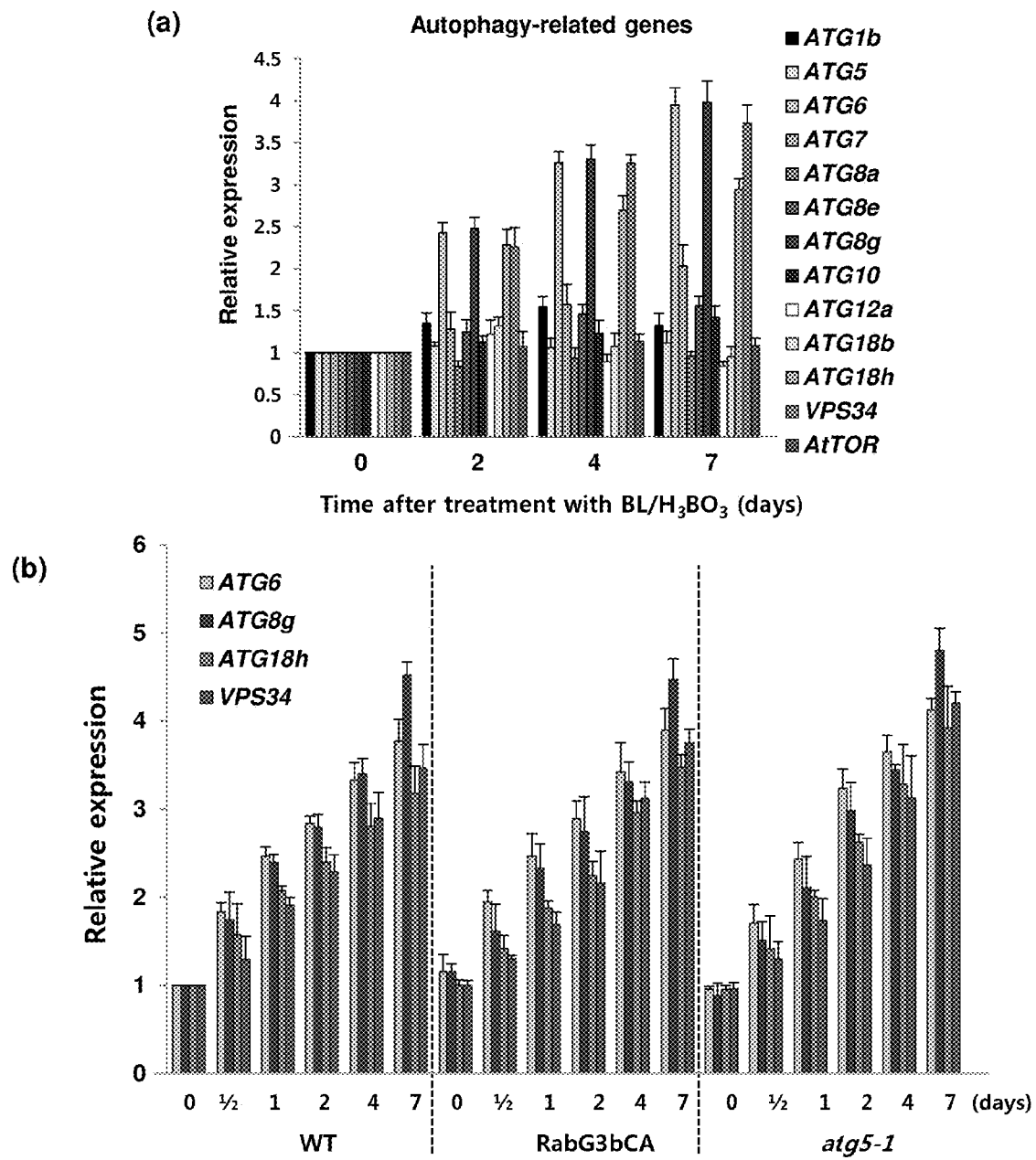

FIG. 10 is a diagram illustrating expression analysis of autophagy-related genes during TE differentiation.

(a) Relative expression of ATG gene in WT culture cells treated with BL/H$_3$BO$_3$ (b) Relative expression of ATGs (ATG6, 8g, 18h, and VPS34) genes screened from WT, RabG3bCA, and atg5-1 culture cells which are treated with BL/H$_3$BO$_3$ The results are represented by means±SE of three independent experiments.

FIG. 11 is a diagram illustrating expression analysis of secondary cell wall-related gene and PCD-related gene during TE differentiation.

(a,b) Relative expression of PCD-related genes (XCP1, AtMC9, and BFN1) (a) and secondary cell wall-related genes (IRX1, 5, 12, and FRA8) (b) screened from WT, RabG3bCA, and atg5-1 culture cells which are treated with BL/H$_3$BO$_3$.

The results are represented by means±SE of three independent experiments.

Figure 12:
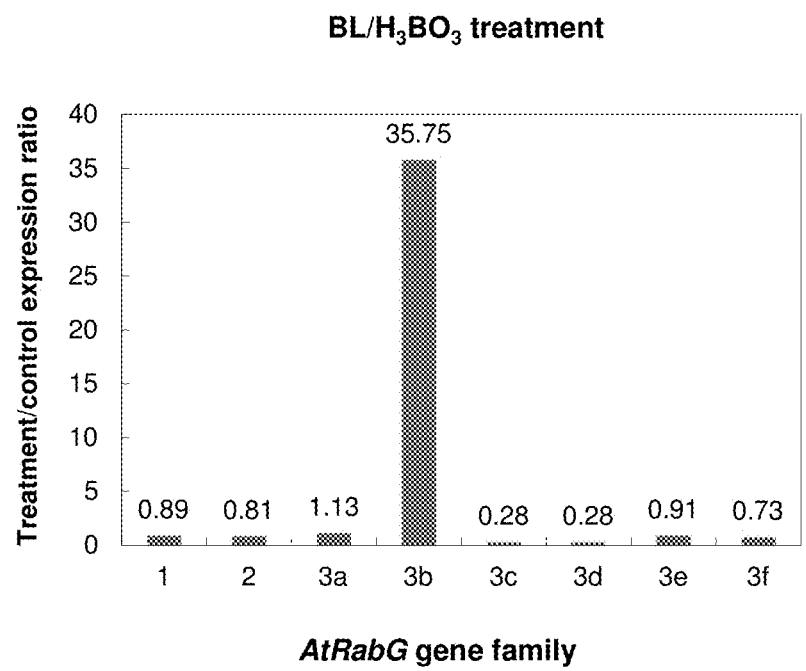

FIG. 12 is a diagram illustrating expression analysis of Arabidopsis RabG genes in EBL/H$_3$BO$_3$ treatment. 1, RabG1 2, RabG2 3a, RabG3a 3b, RabG3b 3c, RabG3c 3d, RabG3d 3e, RabG3e 3f, RabG3f FIG. 13 is a diagram illustrating expression analysis of RabG3b in WT and two independent RabG3bRNAi cell lines.

(a) RT-PCR analysis of a member of RabG3 gene family. Actin is used as the control.

(b) Western blotting analysis of RabG3b protein. The total proteins are separated by SDS electrophoresis and Ponceau S staining (lower end) and Western blotting analysis (upper end) with anti-RabG3b antibody are conducted.

Figure 14:
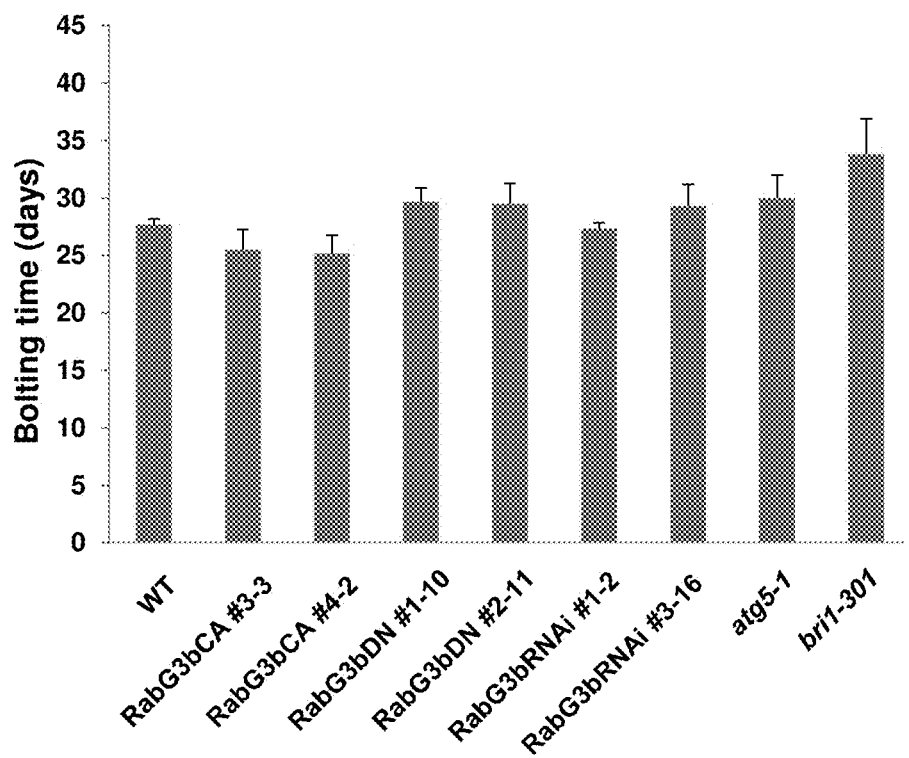

FIG. 14 is a diagram illustrating a bolting time in WT, RabG3bCA, RabG3bDN, RabG3bRNAi, atg5-1, and bri1-301 plants. This experiment is repeated three with similar results (n=10).

Figure 15:
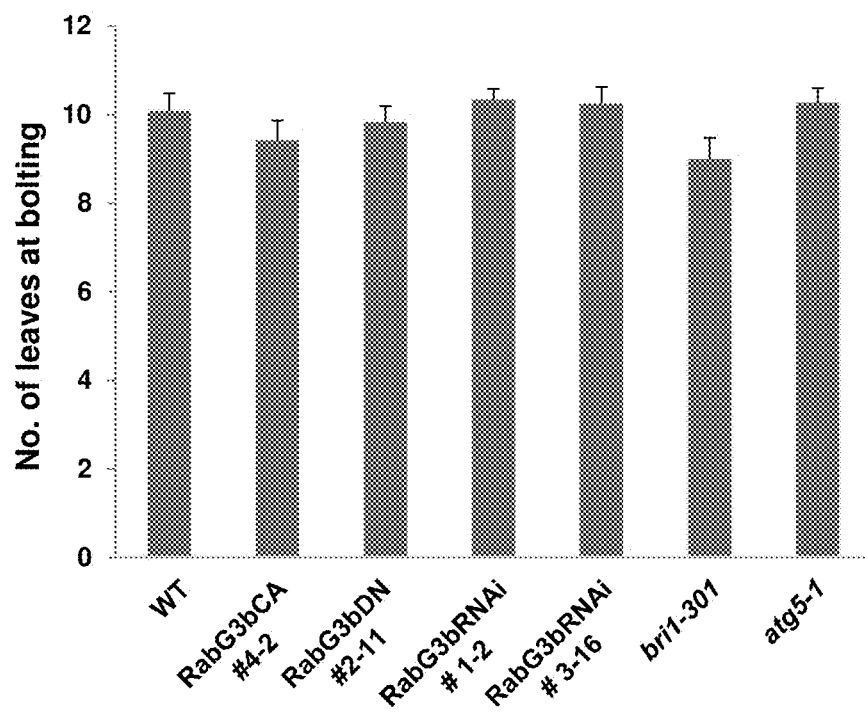

FIG. 15 is a diagram illustrating the total number of leaf in bolted WT, RabG3bCA, RabG3bDN, RabG3bRNAi, atg5-1, and bri1-301 plants.

This experiment is repeated three with similar results (n=10).

Figure 16:
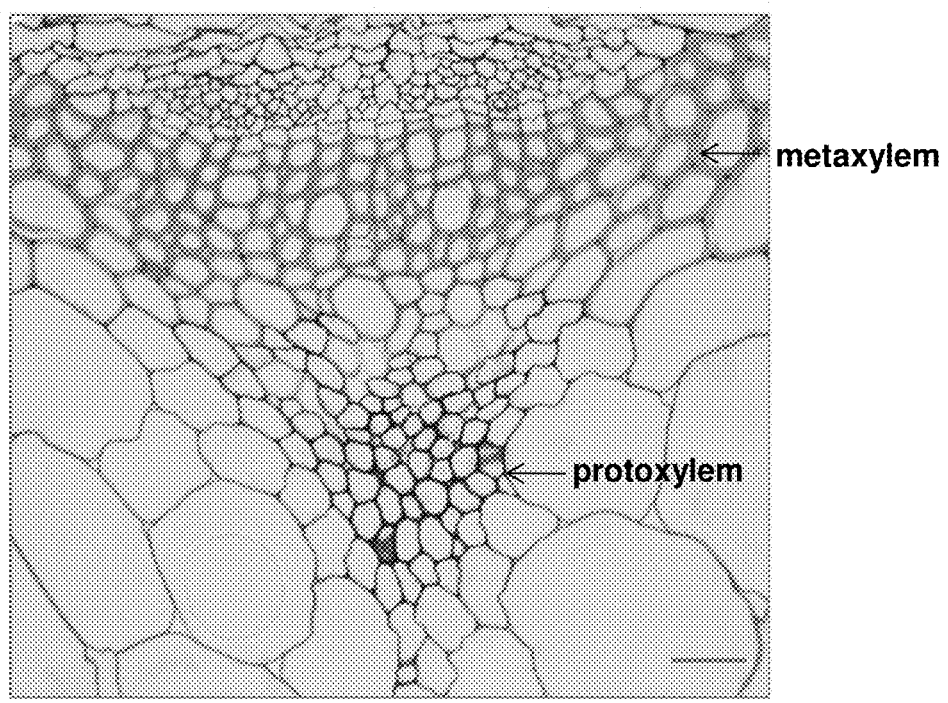

FIG. 16 is a diagram illustrating an example of cells counted from a cross section of an inflorescence stem of a RabG3bCA plant. Metaxylem and protoxylem cells are represented by pink and green, respectively.

Bar=50 μm.

Figure 17:
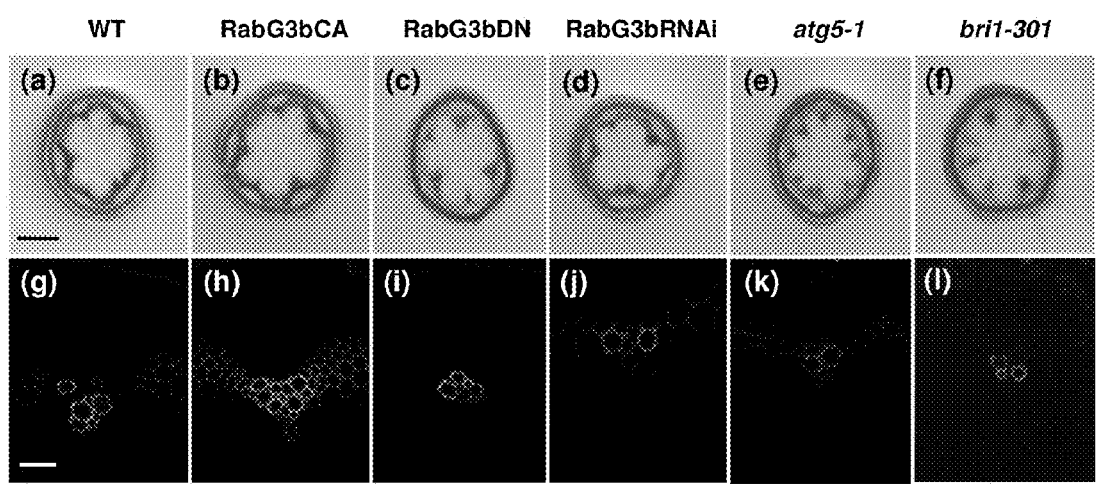

FIG. 17 is a diagram illustrating development of xylem in WT, RabG3bCA, RabG3bDN, RabG3bRNAi, atg5-1, and bri1-301 plants.

(a-f) Cross-sections of inflorescence stems of 6-week-old plants showing a lignified xylem cells stained with phloroglucinol-HCl. Bar=0.2 mm.

(g-l) Cross-sections of inflorescence stems of 6-week-old plants showing lignified xylem cells identified by autofluorescence. Bar=20 μm.

Figure 18:
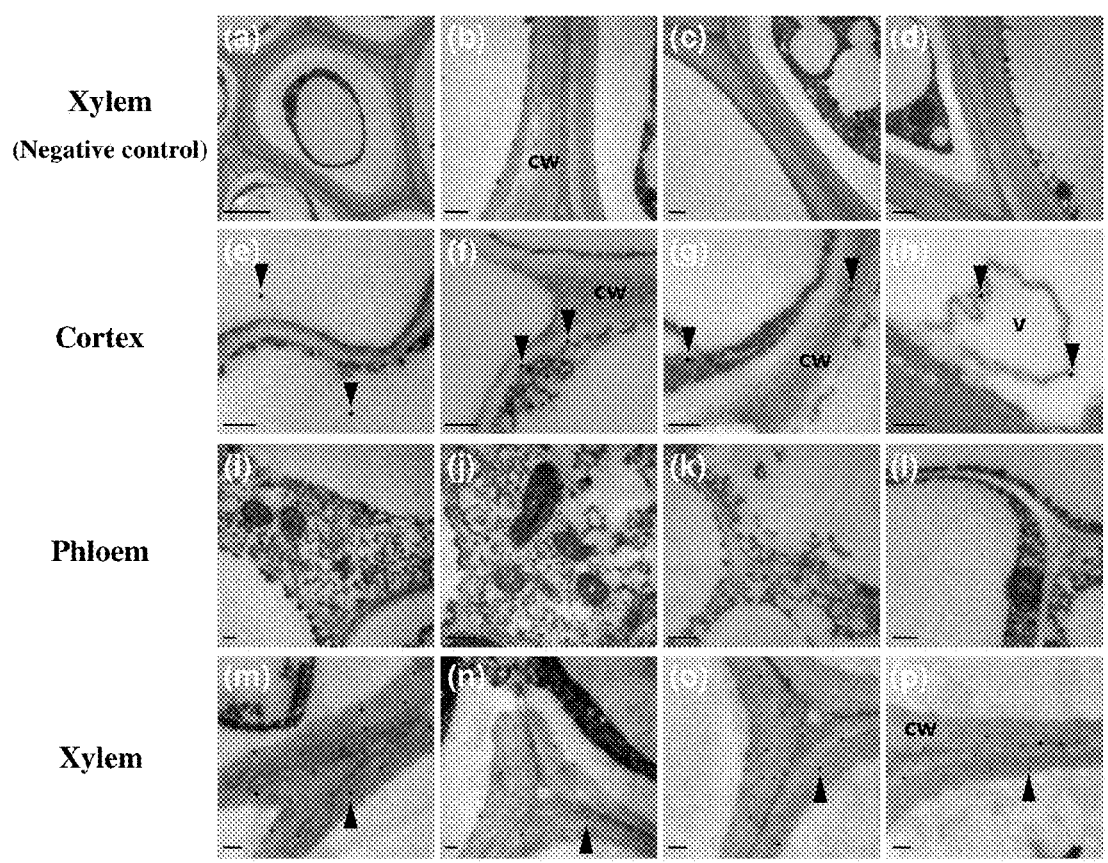

FIG. 18 is a diagram illustrating immunolocalization in inflorescence stem of the WT plant.

In a lower-end portion of the inflorescence stem of the 6-week-old WT plant, the cross section is used for immunolocation of RabG3b protein. For a negative control, preimmune serum is used as the label. An arrow head represents gold particle integrated to RabG3b. CW: cell wall; V: vacuole. Bar=1 μm (a-d) and 0.2 μm (e-p).

Figure 19:
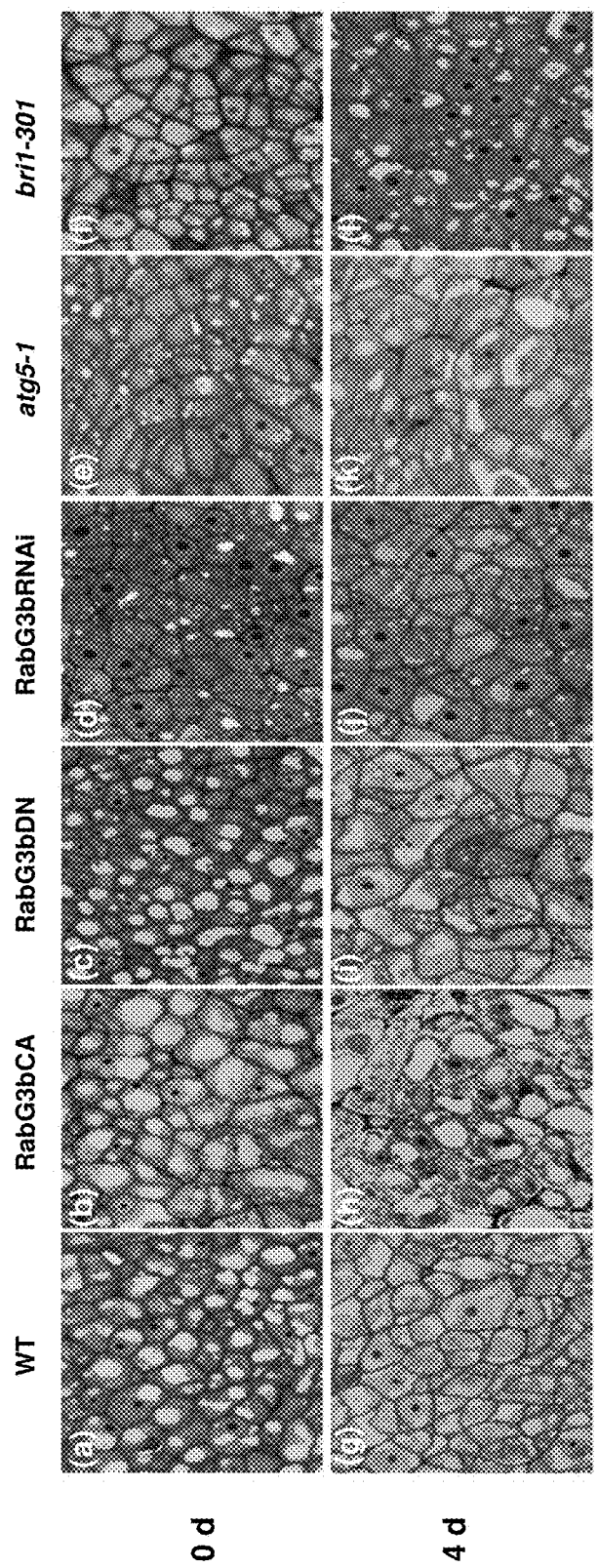

FIG. 19 is a diagram illustrating TE differentiation of cells cultured from WT, RabG3bCA, RabG3bDN, RabG3bRNAi, atg5-1, and bri1-301 plants.

(a-l) Microscopic images of culture cells in which TEs are differentiated. The culture cells are stained with Toluidine blue after 0 (a-f) and 4 (g-l) days of BL/H$_3$BO$_3$ treatment. Bar=10 μm.

Figure 20:
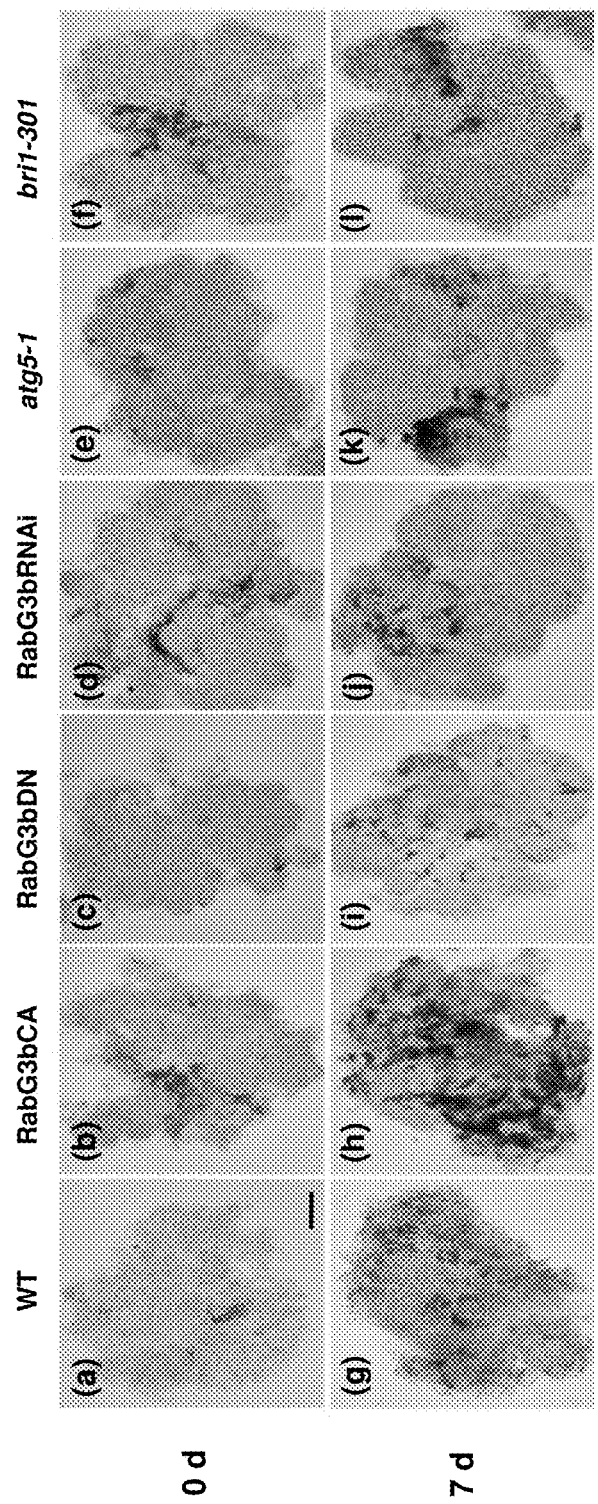

FIG. 20 is a diagram illustrating TE differentiation of cells cultured from WT, RabG3bCA, RabG3bDN, RabG3bRNAi, atg5-1, and bri1-301 plants.

(a-l) TE lignified in culture cells. The culture cells are stained with phloroglucinol-HCl after 0 (a-f) and 7 days (g-l) of BL/H$_3$BO$_3$ treatment. Bar=0.1 mm.

Figure 21:
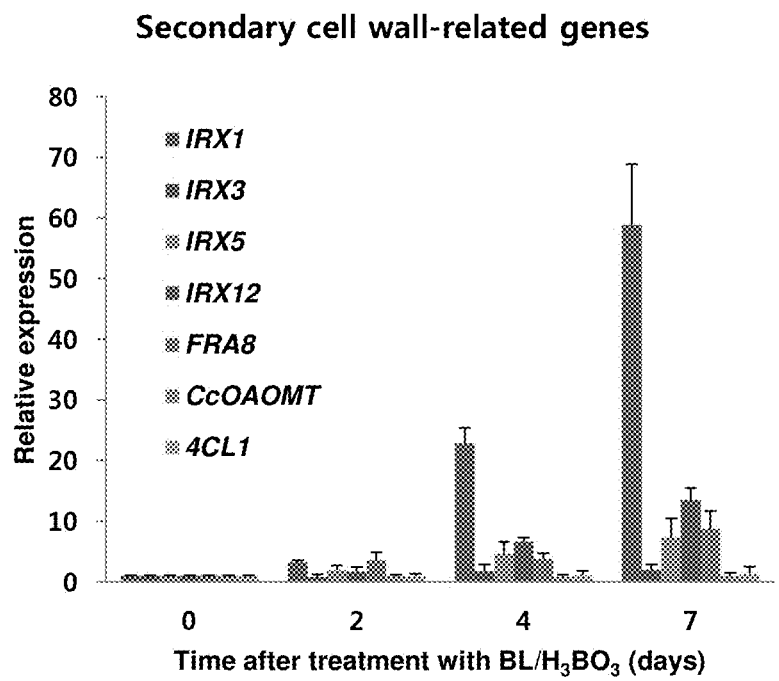

FIG. 21 is a diagram illustrating expression analysis of secondary cell wall-related genes during TE differentiation.

The results are represented by means±SE of three independent experiments.

Figure 22:
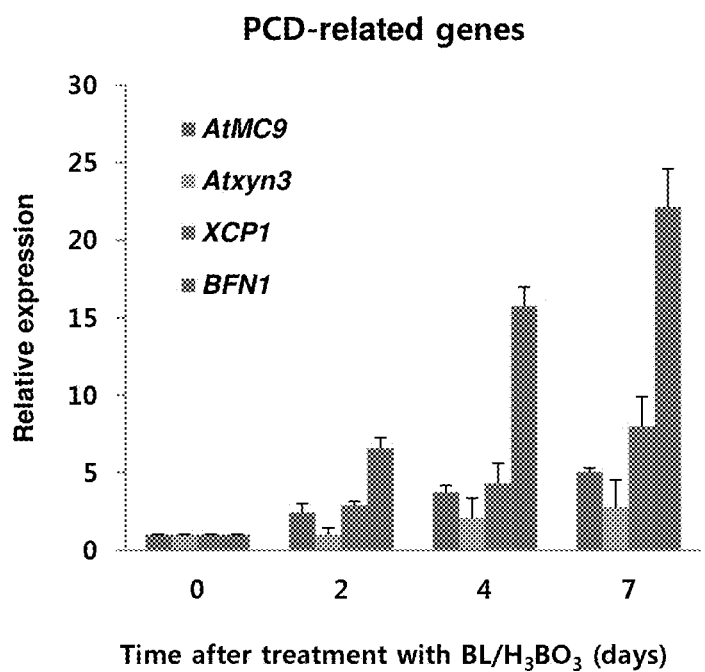

FIG. 22 is a diagram illustrating expression analysis of PCD-related genes during TE differentiation.

The results are represented by means±SE of three independent experiments.

FIG. 23 is a diagram illustrating expression analysis of vascular system-related transcription factors during TE differentiation.

(a) Relative expression of vascular system-related transcription factors in WT culture cells treated with BL/H$_3$BO$_3$.

(b) Relative expression of vascular system-related transcription factor genes (AtHB8, REV, and VND7) in WT, RabG3bCA, and atg5-1 culture cells which are treated with BL/H$_3$BO$_3$.

The results are represented by means±SE of three independent experiments.

FIG. 24 is a diagram illustrating expression analysis of BR-related genes during TE differentiation.

(a) Relative expression of BR-related genes in WT culture cells which are treated with BL/H$_3$BO$_3$.

(b) Relative expression of BR-related genes in WT, RabG3bCA, and atg5-1 culture cells which are treated with BL/H$_3$BO$_3$.

The results are represented by means±SE of three independent experiments.

Figure 25:
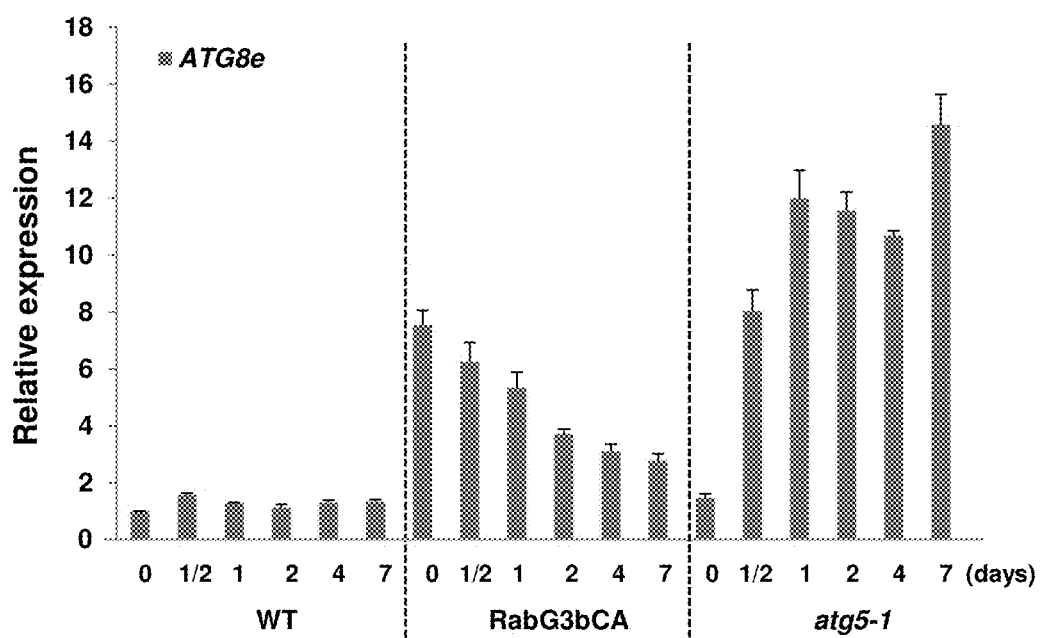

FIG. 25 is a diagram illustrating expression analysis of ATG8e gene during TE differentiation.

The total RNAs are extracted at given times from WT, RabG3bCA, and atg5-1 culture cells, which are treated with BL/H$_3$BO$_3$ and are subjected to real-time qRT-PCR analysis. The results are represented by means±SE of three independent experiments.

Figure 26:
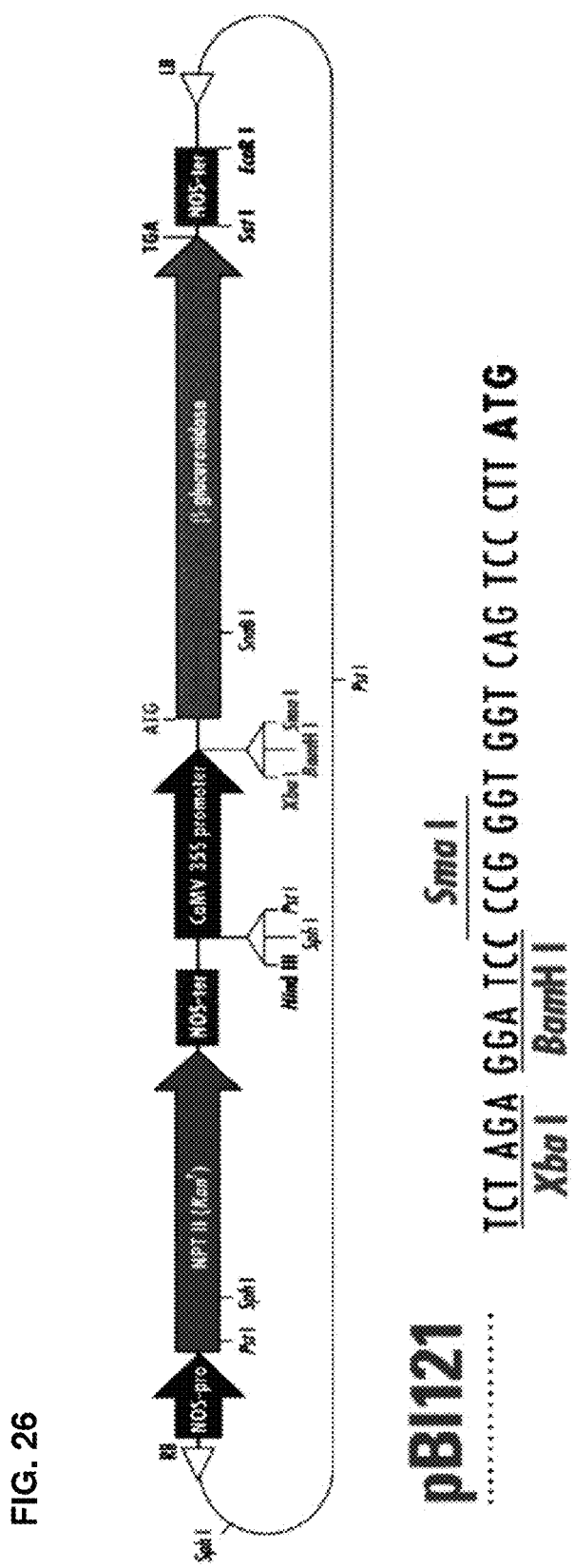

FIG. 26 is a diagram illustrating a cleavage map of an expression vector.

DETAILED DESCRIPTION OF THE PREFERRED EMBODIMENT

Exemplary embodiments of the present invention will now be described in detail with reference to the accompanying drawings.

Hereinafter, exemplary embodiments of the present invention will now be described in detail with reference to the accompanying drawings. However, preferred embodiments are described to illustrate the present invention, but the scope of the present invention is not limited to the embodiments disclosed hereinafter.

Example 1

Plant Material and Growth Condition

*Arabidopsis thaliana* plants were grown at 24° C. in a growth room under long-day conditions (16-h light/8-h dark cycle). *Arabidopsis* callus were formed from seed leaves of young seedlings in an induction medium (Murashige and Skoog [MS] medium, pH 5.8, 3% sucrose, 0.8% agar and 2 mg/l 2,4-dichlorophenoxyacetic acid (2,4-D)). A suspension cell culture was initiated by inoculating 1 to 2 g of callus into 50 ml of MS medium supplemented with 3% sucrose and 1 mg/l 2,4-D, and subcultured at 24° C. in a dark room while stirring. For the TE induction, the subcultured cells were transferred into a 2,4-D-free fresh medium containing 1 μM BL and 10 mM H$_3$BO$_3$. Aliquots were taken at given times for further analysis. In order to induce the sucrose starvation, 1-week-old seedlings grown on the MS (1% sucrose) medium were transferred to a MS medium without sucrose and further grown in a dark room. Plants were harvested 0, 1, and 2 days after their transfer (Contento et al., 2005).

Example 2

Generation of RabG3b Knockdown Plants

An Agrikola RNAi knockdown delivery clone (CATMA1a21795) of RabG3b was purchased from Nottingham *Arabidopsis* Stock Centre (NASC). The construct was transformed into *Arabidopsis* through vacuum infiltration using *Agrobacterium tumefaciens* strain GV3101 (Clough and Bent, 1998). Transformants (T$_1$) were screened based on BASTA resistance. T$_3$ homozygous lines were recovered and tested for reduction of RabG3b expression. Two independent lines (#1-2 and #3-16) were used for further analysis.

Example 3

RNA Analysis

Quantitative real-time RT-PCR was performed in a Light-Cycler 480 system (Roche) using a KAPA SYBR FAST qPCR master mix. PCR reaction was performed according to the manufacturer's protocol. The gene-specific primers used in the present invention are listed in the following Table 1. The expression of the tested genes was standardized to the constitutive expression level of UBQ5, and calculated using the $2^{-\Delta\Delta t}$ method (Livak and Schmittgen, 2001). This experiment was repeated at least three times with biologically independent samples.

TABLE 1

| Genes | Accession numbers | Forward primers | Reverse primers |
|---|---|---|---|
| For RT-PCR | | | |
| RabG3a | At4g09720 | GATAAGAAAGCAGCTGACTGGTGT (SEQ ID NO: 4) | GATCATACACAGACTTCTCCAATC (SEQ ID NO: 5) |
| RabG3b | At1g22740 | AGAAGGCTAGAGAATGGTGTGCT (SEQ ID NO: 6) | GACATACAAATCGTGAACCACCAAATG (SEQ ID NO: 7) |
| RabG3c | At3g16100 | AGATGGAGTCAATGTTGATGCAGCT (SEQ ID NO: 8) | GAAGATTACGACAAGCTGAAGAGAT (SEQ ID NO: 9) |
| RabG3d | At1g52280 | CGCCAAAGAAGGATTCAATGTAGA (SEQ ID NO: 10) | GAGTCCAAAAGAAAAAGGAACCCA (SEQ ID NO: 11) |
| Actin | | GGCGATGAAGCTCAATCCAAACG (SEQ ID NO: 12) | GGTCACGACCAGCAAGATCAAGACG (SEQ ID NO: 13) |
| For real-time qRT-PCR | | | |
| IRX1 | At4g1g780 | CATCCCAACGCTATCAAACCTA (SEQ ID NO: 14) | GCTGAGACACCTCCAATAACCC (SEQ ID NO: 15) |
| IRX3 | At5g17420 | TCGGTGGCATGATGAATTTG (SEQ ID NO: 16) | CACATCTATACCACTTCTTGCCTACTG (SEQ ID NO: 17) |
| IRX5 | At5g44030 | TCTGGGTGATTGGCGGTG (SEQ ID NO: 18) | GTCGGAGGGATGAGAAGGGT (SEQ ID NO: 19) |
| IRX12 | At2g38030 | CCTAAGGATCTTCCCAAGTGCTAA (SEQ ID NO: 20) | CTTGGACGTGGCGTGATGT (SEQ ID NO: 21) |
| VND6 | At5g62380 | GAAAATGGACCGCCTCATGA (SEQ ID NO: 22) | TCATCGTGGTTAGCTTCTTCTTGA (SEQ ID NO: 23) |
| VND7 | At1g71930 | TTCGAAACGCAGTCGTATAATCC (SEQ ID NO: 24) | ATTAGCTTCGACCTCATTATAGCTTTG (SEQ ID NO: 25) |
| XCP1 | At4g35350 | GTTGTGCTTTTGCCCGTGAT (SEQ ID NO: 26) | GAAGCTTGTCAGTGTTTGTCAAATG (SEQ ID NO: 27) |
| AtXyn3 | At4g08160 | CCACCTCCACGAGCTGACATTC (SEQ ID NO: 28) | AAGGAGGAGGCGATGGACGATTC (SEQ ID NO: 29) |
| AtMC9 | At5g04200 | AGGCAGTCCTTGACCACTTG (SEQ ID NO: 30) | CCCTGAGTCCACGTGTTTTT (SEQ ID NO: 31) |
| ATG1a | At1g49180 | TGCCACACTGGGCATAGAAGAT (SEQ ID NO: 32) | TCCAGTTACACGAGCCATTTCA (SEQ ID NO: 33) |
| ATG1b | At2g37840 | ATTCTGAATCCGCCACTGTC (SEQ ID NO: 34) | GAGAACCCAACCCAAGTGAA (SEQ ID NO: 35) |
| ATG1c | At3g53930 | GAAATATCAGCCACGGAGGA (SEQ ID NO: 36) | GCACCGCTTTTGAGTAGAGG (SEQ ID NO: 37) |
| ATG1d | At3g61960 | GAAACAAGTGCTGCCACTCA (SEQ ID NO: 38) | AATCCGCTTCTTGTCGTCAG (SEQ ID NO: 39) |
| ATG5 | At5g17290 | TTAATCGCCCTGTTGAGTTCCTCA (SEQ ID NO: 40) | TACCACCCACGAAAACGGTATCTC (SEQ ID NO: 41) |
| ATG6 | At3g61710 | TTGCAAATTCAAAGGACCAAGAGA (SEQ ID NO: 42) | AGAGAGACCGTCGCAGAGAGAGGT (SEQ ID NO: 43) |

TABLE 1-continued

| Genes | Accession numbers | Forward primers | Reverse primers |
|---|---|---|---|
| ATG7 | At5g45900 | GTACCGCTTGCTCTGAAACC (SEQ ID NO: 44) | GTCTTCCCAGTCGAGGTTGA (SEQ ID NO: 45) |
| ATG8a | At4g21980 | GGAGAAGGCTGGACAAAGTGATGT (SEQ ID NO: 46) | TAGATCGCAGACATCAATGCAGCA (SEQ ID NO: 47) |
| ATG8e | At5g05150 | ACCCTGATCGAATTCCTGTGATTG (SEQ ID NO: 48) | AGCTCTCCTGTTGGAGGAAGAACA (SEQ ID NO: 49) |
| ATG8g | At3g60640 | ACCGGAGCGATGATGTCAACCATT (SEQ ID NO: 50) | TGCAAACCGATTGGTTGTGCCTAC (SEQ ID NO: 51) |
| ATG10 | At3g07525 | CCCAACCATGGAAAATGAAG (SEQ ID NO: 52) | GAACCATGGCCTGTTCAAAT (SEQ ID NO: 53) |
| ATG12a | At1g54210 | GCATGGGGCTAAAACTGAAG (SEQ ID NO: 54) | GCCGACGGAAAAATACAAAG (SEQ ID NO: 55) |
| ATG18b | At4g30510 | TTTGGACCATCGACACAGCTTCCA (SEQ ID NO: 56) | ACTGCGTTTTGAAGCACATGATGA (SEQ ID NO: 57) |
| ATG18d | At3g56440 | TGACCTTGACATTGGATGGCTTGC (SEQ ID NO: 58) | TTGATACTGCAAGCCACTGCACGT (SEQ ID NO: 59) |
| ATG18h | At1g54710 | ACGCTCATGTCTTGCCAAAGAACG (SEQ ID NO: 60) | TTTCATTGGAGACCACCTCCTCGA (SEQ ID NO: 61) |
| VPS34 | At1g60490 | AGACACCTGGACAACCTCCTCCTT (SEQ ID NO: 62) | GGAATAGTTGAACCCGCCATGAGA (SEQ ID NO: 63) |
| AtTOR | At1g50030 | TGAAGTCCCCCAATTAGCAC (SEQ ID NO: 64) | ACGGCACGCTCATTTAAAAC (SEQ ID NO: 65) |
| BRI1 | At4g39400 | GATTCACCGGATTTTGGAGA (SEQ ID NO: 66) | GACCCGGCTTGTATCTCCTT (SEQ ID NO: 67) |
| BRL1 | At1g55610 | TTGATCCGGAGCTTGTAACC (SEQ ID NO: 68) | CCTTATCTCGCGATTCTTCG (SEQ ID NO: 69) |
| BRL2 | At2g01950 | CGAGACTGATCAGCGCATTA (SEQ ID NO: 70) | TTTCCCTTCTCTTGCCTTCA (SEQ ID NO: 71) |
| BRL3 | At3g13380 | GAGCTCCTCTCAGGCAAGAA (SEQ ID NO: 72) | CGATCGTCCAAACATTGAGA (SEQ ID NO: 73) |
| AtHB8 | At4g32880 | AATCATTCCTTCCGGTTTCC (SEQ ID NO: 74) | CGACGCGATCACACTTCTTA (SEQ ID NO: 75) |
| AtHB15 | At1g52150 | GCGGGATATGTCTCTCAAGC (SEQ ID NO: 76) | TACAGCCAAAAGGCAAAAGC (SEQ ID NO: 77) |
| PHB | At2g34710 | GCTTCACCGGTTTTCACATT (SEQ ID NO: 78) | AGAACTTTCCACACCGTTGC (SEQ ID NO: 79) |
| PHV | At1g30490 | CTTCCGGCAGGAATATGTGT (SEQ ID NO: 80) | GCCAAAACAACATCCCCTA (SEQ ID NO: 81) |
| REV | At5g60690 | ATTCACTTGGAAGCGACGAC (SEQ ID NO: 82) | GCGAAGTCCGAACAGATAGC (SEQ ID NO: 83) |
| FRA8 | At2g28110 | GACTTGTTGAATCGGTGGCTC (SEQ ID NO: 84) | GAAAGAGTTTGACCTTCTAAC (SEQ ID NO: 85) |
| CCoAOMT | At4g34050 | TCGTTGATGCTGACAAAGACA (SEQ ID NO: 86) | ACTGATGCGACGGCAGATAG (SEQ ID NO: 87) |
| 4CL1 | At1g51680 | GGTTACCTCAACAATCCGGCA (SEQ ID NO: 88) | CAAATGCAACAGGAACTTCAC (SEQ ID NO: 89) |
| BFN1 | At1g11190 | CGTGGACAGAATGCAACGATC (SEQ ID NO: 90) | ACCAGCAATAGCATGATCGTC (SEQ ID NO: 91) |
| UBQ5 | At3g62250 | GACGCTTCATCTCGTCC (SEQ ID NO: 92) | GTAAACGTAGGTGAGTCCA (SEQ ID NO: 93) |

Example 4

Histochemical Analysis

Plant samples (cultured cells and inflorescence stems of 7-week-old plants) were fixed at 4° C. for 4 hours in a solution containing 2.5% glutaraldehyde and 4% para-formaldehyde in 0.1 M phosphate buffer (pH 7.4), rinsed in 0.1 M phosphate buffer (pH 7.4), and further fixed at room temperature for 2 hours in 1% $OsO_4$. After rinsing in the 0.1M phosphate buffer, the resulting samples were dehydrated and embedded in a LR white resin (London Resin).

Cross-sections (1 μm) were prepared using an ultramicrotome (RMC MT X) and stained briefly with filtered 1% Toluidine blue. These sections were photographed using a light microscope (Olympus, BX51TRF), and images were used to measure stem thickness and count protoxylem and metaxylem cells within vascular bundles (n=10).

For TEM analysis, thinner sections (60-70 nm thickness) were collected on copper grids (1-GN, 150 mesh), stained with uranyl acetate and lead citrate, and examined by TEM (Philips, Tecnai 12).

For immunolocalization, the sections collected on the nickel grids were blocked for 1 hour with a BSA-TBS buffer (500 mM NaCl, 1% BSA, 0.3% Tween 20, and 10 mM Tris-HCl, pH 7.4). The sections were then incubated with anti-RabG3b antiserum (rabbit) and/or anti-ATG8e antiserum (rat) for 4 hours at room temperature. After rinsing in the BSA-TBS buffer, binding of the primary antibody was detected using anti-rabbit IgG (20-nm gold, Electron Microscopy Sciences) and anti-rat IgG (1-nm gold, Sigma). After washing in the BSA-TBS and deionized water, the resulting samples were stained with uranyl acetate before TEM analysis.

Example 5

Lignin Staining

Lignin staining was performed in the same manner as described in the previous studies (see: Protoplasma 220, 17-28, Pomar et al., 2002). In order to stain the inflorescence stems, cross-sections from the middle region of the inflorescence stems from the 6-week-old plants were prepared by cutting the middle region with a razor blade. The sections and cultured cells were then stained in a phloroglucinol solution (2% ethanol/water, 95/5 (v/v)) for 1 minute and soaked in 6 N HCl. Bright field photographs of the stained inflorescence stem samples and the cell culture samples were collected using a binocular microscope (Leica EZ4D) and a light microscope (Olympus, BX51TRF), respectively. Autofluorescence of lignin was detected using a confocal microscope (Zeiss LSM 510 META) as excited/emitted at 420/480 nm.

Example 6

LTG Staining

LTG staining was performed in the same manner as described in the previous studies (see: Cell, 121, 567-577, Liu et al., 2005). Cultured cells were incubated for 1 hour with 1 μM LTG DND-26 (Molecular Probes) in a dark room. Images were obtained using a confocal microscope (Zeiss LSM 510 META) as excited/emitted at 488/505 nm.

As seen according to the present invention, when the RabG3b genes according to the present invention are overexpressed, the promotion of biomass was observed, in comparison with the wild type. As seen from these effects, it was revealed that, in the RabG3bCA cells, a small GTP binding protein RabG3b continue to activate the autophagy and this activation of the autophagy is performed through accumulation of a large number of autophagic vacuoles and lysosomes.

While the present invention has been shown and described in connection with the exemplary embodiments, it will be apparent to those skilled in the art that modifications and variations may be made without departing from the scope of the invention as defined by the appended claims.

What is claimed is:

1. A method for promoting late stage xylem development of a plant comprising:
   overexpressing a gene encoding a mutant RabG3b protein in the plant, wherein the mutant RabG3b protein comprises the amino acid sequence SEQ ID NO: 1 having a leucine at the 67th residue of the sequence SEQ ID NO: 1; and
   selecting a plant having a phenotype of promoted tracheary element differentiation compared to the wild-type.

2. The method according to claim 1, wherein the gene encoding a mutant RabG3b protein has the DNA sequence set forth in SEQ ID NO: 3.

3. The method according to claim 1, wherein the promoted tracheary element differentiation is evaluated by increase of the number of xylem cells.

4. The method according to claim 1, wherein the promoted tracheary element differentiation is evaluated by expansion of lignified cell walls.

* * * * *